US008298783B2

(12) United States Patent
Baker

(10) Patent No.: US 8,298,783 B2
(45) Date of Patent: Oct. 30, 2012

(54) DETECTING MOLECULES

(75) Inventor: Mark S. Baker, Sydney (AU)

(73) Assignee: Macquarie University, North RydeNew South Wales (AU)

( * ) Notice: Subject to any disclaimer, the term of this patent is extended or adjusted under 35 U.S.C. 154(b) by 1297 days.

(21) Appl. No.: 10/569,107

(22) PCT Filed: Aug. 20, 2004

(86) PCT No.: PCT/AU2004/001123
§ 371 (c)(1),
(2), (4) Date: Apr. 2, 2007

(87) PCT Pub. No.: WO2005/019243
PCT Pub. Date: Mar. 3, 2005

(65) Prior Publication Data
US 2007/0190569 A1 Aug. 16, 2007

(30) Foreign Application Priority Data

Aug. 21, 2003 (AU) ................................ 2003904694
Jun. 2, 2004 (AU) ................................ 2004902935

(51) Int. Cl.
G01N 33/53 (2006.01)
G01N 31/00 (2006.01)
(52) U.S. Cl. ........ 435/7.21; 435/7.1; 436/501; 436/518; 422/50
(58) Field of Classification Search .......................... None
See application file for complete search history.

(56) References Cited

U.S. PATENT DOCUMENTS

| | | | |
|---|---|---|---|
| 4,550,019 A | 10/1985 | Polson | |
| 4,568,488 A | 2/1986 | Lee-Huang | |
| 5,173,422 A * | 12/1992 | Knowles et al. | 435/331 |
| 5,367,054 A | 11/1994 | Lee | |
| 5,420,253 A | 5/1995 | Emery et al. | |
| 2002/0127739 A1 * | 9/2002 | Pieper et al. | 436/515 |
| 2003/0032017 A1 | 2/2003 | Anderson et al. | |

FOREIGN PATENT DOCUMENTS

| | | |
|---|---|---|
| DE | 196 50 991 A1 | 6/1998 |
| WO | WO 02/055654 A2 * | 7/2002 |
| WO | WO 2005/019243 A1 | 3/2005 |

OTHER PUBLICATIONS

Gassmann et al. FASEB, vol. 4, pp. 2528-2532, 1990.*
Sleister, H.M. et al. "Subtractive immunization: a tool for the generation of discriminatory antibodies to proteins of similar sequence", J.Immuno.Methods (2002) pp. 213-220.
Shefcheck, K. et al. "Fractionation of cytostic proteins on an immobilized heparin column" Anal.Chem., Apr. 1, 2003, 75 (7)(1691-8).
Gorg. A., et al., Sample prefractionation with Sephadex isoelectric focusing prior to narrow pH range two-dimensional gels:, Proteomics 2002, 12, 1652-1657.
Badcock V, et al., "Prefractionation of protein samples for proteome analysis using reversed-phase high performance liquid chromatography", Electrophoresis, 2001, 14, 2856-2864.
Huang Hong-Lei et al. "Enrichment of low-abundant serum proteins by albumin/immunoglobulin G immunoaffinity depletion under partly denaturing conditions" Electrophoresis (2005) 2843-2849.
Vonwirth H. et al. "Serological analysis and characterization of calf thymus ribonuclease H IIb" European J. of Biochem./FEBS (1989)184(2) 321-329.
Kuhn E. et al. "Quantification of C-reactive protein in the serum of patients with rheumatoid arthritis using multiple reaction monitoring mass spectrometry and 13C labeled peptide standards" Proteomics (2004) 4, 1175-1186.
Xu, J. et al, "Generation of monoclonal antibodies to cryptic collagen sites by using subtractive immunization" Hybridoma (2000) (5) 375-385.
Akita E.M., et al., "Isolation of bovine immunoglobulin G subclasses from milk, colostrum, and whey using immobilized egg yolk antibodies," J Dairy Science, American Dairy Science Association, Savoy, IL, USA, (Jan. 1998) 81(1):54-63.
Allen, S.H., et al., "Purification of alpha-fetoprotein from human cord serum with demonstration of its antiestrogenic activity," Biochimica et Biophysica Acta, (1993) 1202(1):135-142.
Baxter, R., "Circulating levels and molecular distribution of the acid-labile (alpha) subunit of the high molecular weight insulin-like growth factor-binding protein complex," Journal of Clinical Endocrinology and Metabolism, (1990) 70(5):1347-1353.
Daly M.B., et al., "The search for predictive patterns in ovarian cancer: Protromics meets bioinformatics," Cancer Cell, (Mar. 2002) 1:111-112.
Davidsson, P., et al., "A new procedure for detecting brain-specific proteins in cerebrospinal fluid," J of Neural Transm, (1997) 104(6-7):711-720.
Gassman M., et al., "Efficient production of chicken egg yolk antibodies against a conserved mammalian protein," FASEB J., (1990) 4:2528-2532.
Georgiou, H.M., et al., "Proteomic analysis of human plasma: Failure of centrifugal ultrafiltration to remove albumin and other high molecular weight proteins," Proteomics, (2001) 1:1503-1506.
Hage, D.S., "Affinity chromatography," In Katz E Eksteen R Shoenmakers P Miller N eds. Handbook of HPLC (1998) 483-498 (Marcel Dekker, New York).

(Continued)

Primary Examiner — Lisa Cook
(74) Attorney, Agent, or Firm — Richard F. Trecartin; Morgan Lewis & Bockius LLP

(57) ABSTRACT

Disclosed are processes to increase the relative abundance of a molecule that is present in a test sample at relatively low abundance. The process includes fractionating a sample and immunizing hosts with the fractions. The antibodies produced from the fractionated test sample are directed primarily to molecules that are in relatively high abundance in the test sample fractions. These antibodies are then contacted with the test sample or a test sample to immuno-deplete relatively high abundance molecules from the sample to form a first depleted sample. These steps can be repeated a reiterative process of immuno-subtraction to produce second and third depleted samples where the relative abundance of the "low abundance" molecule is increased.

25 Claims, 13 Drawing Sheets

OTHER PUBLICATIONS

Hage, D.S., "Survey of recent advances in analytical applications of immunoaffinity chromatography," *J. Chromatogr B* (1998) 715:3-28.

Hage, D.S., "Affinity chromatograph: A review of clinical applications," *Clinical Chemistry* (1999) 45(5):593-615.

Jones K., "A review of biotechnology and large scale affinity chromatography," *Chromatographia*, (Nov. 1991) 32(9/10):469-480.

Kim, H.-O., et al., "Reusability of avidin-biotinylated immunoglobulin Y columns in immunoaffinity chromatography," *Analytical Biochemistry*, Academic Press, San Diego, CA, USA (Mar. 1999) 268(2):383-397.

Larsson, P.-O., "High-performance liquid affinity chromatography," *Methods Enzymol*, (1984) 104:212-223.

Larsson, A., et al., "Chicken IgY: Utilizing the evolutionary difference," *Comp. Immun. Microbiol. Infect. Dis.*, (1990) 13(4):199-201.

Larsson, A., et al., "Antibody response in laying hens with small amounts of antigen," *Food and Agricultural Immunology*, (Mar. 1998) 10(1):29-36.

Lee K A., et al., "Acid stability of anti-*Hellobacter pyroli* IgY in aqueous polyol solution," *J Biochem Mol Biol*, (Sep. 2002) 35(5):488-493.

Lollo, B.A., et al., "Improved two-dimensional gel electrophoresis representation of serum proteins by using protoclear™," *Electrophoresis*, Wiley-VCH Verlag, Weinheim, DE, (Apr. 1999) 20(4/5):854-859.

Losso, J.N., et al., "Removal of bovine serum albumin from cow's milk using chicken egg-yolk antibodies immobilized on chitosan gel," *Food Science Technology Abstracts*, (1999) 31:230 abstract, [Food and Agricultural Immunology (1998) 10(1):47-56].

Rodriguez-Burgos, A., "Detection in chick embryo of fetoproteins not recognized by the dam's immune system and of soluble alloantigens. Presumptive teratogenic and abortogenic capacity of their specific IgY," *BMC Immunol.*, (2003) 4(6):1-12.

Scawen M.D., "Dye affinity chromatography," *Anal Proc*, (May 1991) 28:143-144.

Sharma, J.M., "The structure and function of the avian immune system," *Acta Veterinaria Hungarica*, (1997) 45(3):229-238.

Shimazaki, Y., et al., "Protein spot recognition on the non-denaturing and denaturing two-dimensional electrophoresis patterns using in situ immunosubtraction via protein A agarose and antibodies," *J Biochem. Biophys. Methods*, (1999) 39:179-184.

Sørensen, S., "Isolation of amniotic fluid proteins of non-maternal serum origin by negative immuno-affinity chromatography," *Clinica Chimica Acta*, (1991) 202(3):199-209.

Berry, Mark J., "Immunoaffinity Purification of Industrally Relevant Enzymes," Analytical Proceedings, v. 28, p. 141-142, May 1991.

Jones, Ken, "Affinity Chromatography—An Overview," Analytical Proceedings, v. 28, p. 140-141, May 1991.

\* cited by examiner

DETECTING MOLECULES

CROSS-REFERENCE TO RELATED APPLICATION

This application is a Section 371 National Stage Application of International Application No. PCT/AU2004/001123, filed 20 Aug. 2004 and published as WO 2005/019243 A1 on 3 Mar. 2005, which claims the priority from the Australian patent application 2003904694, filed 21 Aug. 2003, and Australian patent application 2004902935, filed 2 Jun. 2004, the subject matter of which are hereby incorporated by reference in their entirety.

FIELD OF THE INVENTION

The invention relates to separating molecules, in particular, to proteins comprised in biological fluid such as serum, to purifying molecules and to producing antisera to molecules.

BACKGROUND OF THE INVENTION

One common characteristic of biological samples, such as cell and tissue lysates, serum samples etc. and other complex samples of molecules, is that the molecules comprised in these samples are not represented equally in terms of their relative abundance. For example, albumin constitutes about 50% of the protein in total serum whereas transthyretin constitutes about 0.3%.

One consequence is that, notwithstanding the many techniques for separation of samples of molecules, where two or more molecules have a common characteristic and are separated according to that characteristic, it is difficult to distinguish one molecule from the other. Importantly, it is difficult, and may well indeed be impossible, to detect the molecule that has the lower relative abundance. For example, where molecules are separated according to molecular weight and charge in 2 dimensional gel electrophoresis, it is very difficult to detect a molecule having a low relative abundance in the sample in the circumstance where a molecule having a high relative abundance and the same or similar molecular weight and charge is also present in the sample.

Thus a limitation applies to the applicability of techniques such as 2 dimensional gel electrophoresis for permitting identification of molecules that have a low relative abundance in a sample. This limitation is a significant barrier to the discovery of molecules in fields such as proteomics.

One approach to improving the capacity of 2 dimensional gel electrophoresis for identification of proteins is to deplete molecules from a sample that have a high relative abundance by selecting known or otherwise commercially available antibodies to deplete proteins having a high relative abundance before 2 dimensional gel electrophoresis.

A problem with this approach is that the depletion of high abundance proteins is limited by the content of the panel of known or otherwise commercially available antibodies available for selection. Accordingly, the only high relative abundance proteins that can be depleted are those for which the antibodies are known or are otherwise commercially available. Further, proteins that have a lower relative abundance than those depleted by this approach, and that have a higher relative abundance than the protein of interest, may not be depleted if the antibodies for binding to these proteins are not available.

A further problem is that in many biological fluids, the proteins that have the higher relative abundance may not be known or otherwise, no antibodies may be available to bind to these. Accordingly it is not possible to deplete the proteins having a high relative abundance from these samples using this approach.

Another problem with this approach is that it is expensive and requires a degree of technical manipulation to prepare the known or otherwise commercially available antibodies to be used for depletion. While depletion would be assisted by using antibodies that bind to different epitopes of the same protein, in practice it is very difficult to prepare a composition including more than one antibody for each protein to be depleted, for the depletion of more than one high abundance protein.

There is a need for an improvement in the identification or detection of molecules that have a low relative abundance in a sample.

SUMMARY OF THE INVENTION

The invention seeks to at least minimise one or more of the above problems or limitations and/or to provide an improvement in the identification or detection of molecules and in a first aspect provides a process for increasing the relative abundance of a target molecule in a test sample. The process includes the following steps:

a) utilising the test sample to produce a first group of antibodies for binding to at least one species of molecule in the test sample that has a higher relative abundance in the test sample than the target molecule;

b) utilising the first group of antibodies to deplete from the test sample at least one species of molecule that has a higher relative abundance in the test sample than the target molecule, to produce a first depleted sample;

c) utilising the first depleted sample to produce a second group of antibodies for binding to at least one species of molecule in the first depleted sample that has a higher relative abundance in the first depleted sample than the target molecule; and d) utilising the first and second groups of antibodies to deplete from the test sample at least one species of molecule that has a higher relative abundance in the test sample than the target molecule, to increase the relative abundance of the target molecule in the test sample.

In a second aspect, the invention provides a process for producing a purified form of a target molecule from a test sample. The process includes the following steps:

a) utilising the test sample to produce a first group of antibodies for binding to at least one species of molecule in the test sample that has a higher relative abundance in the test sample than the target molecule;

b) utilising the first group of antibodies to deplete from the test sample at least one species of molecule that has a higher relative abundance in the test sample than the target molecule, to produce a first depleted sample;

c) utilising the first depleted sample to produce a second group of antibodies for binding to at least one species of molecule in the first depleted sample that has a higher relative abundance in the first depleted sample than the target molecule; and d) utilising the first and second groups of antibodies to deplete from the test sample at least one species of molecule that has a higher relative abundance in the test sample than the target molecule, to increase the relative abundance of the target molecule in the test sample.

In a third aspect, the invention provides a purified form of a target molecule. The purified form of the target molecule is characterised in being one produced by the process of the second aspect of the invention.

In a fourth aspect, the invention provides a lit or composition for detecting a ligand or binding partner for a target molecule. The kit includes a purified form of a target molecule of the third aspect of the invention. The purified form of the target molecule may be arranged on a solid phase.

In a fifth aspect, the invention provides a process for producing an antibody that binds to a target molecule having a low relative abundance in a test sample. The process includes the following steps:

a) producing a sample that has a higher relative abundance of the target molecule than the test sample, according to the process of the first aspect of the invention; and b) utilising the produced sample to produce at least one antibody to the target molecule.

In a sixth aspect, the invention provides an antibody that binds to a target molecule. The antibody is characterised in being one produced by the process of the fifth aspect of the invention.

In a seventh aspect, the invention provides a kit or composition for detecting a target molecule. The kit includes an antibody of the sixth aspect of the invention. The antibody may be arranged on a solid phase.

In an eighth aspect, the invention provides a process for increasing the relative abundance of a molecule having a low relative abundance in a test sample. The process includes the following steps:

a) fractionating the test sample according to a property of the molecules of the test sample, to form at least two fractions of the test sample;

b) providing a population of hosts for producing a group of antibodies for binding to molecules of the test sample that have a high relative abundance in each fraction of the test sample;

c) introducing each fraction of the test sample into a host of the population so that each host of the population receives one of the fractions of the test sample, to produce the group of antibodies;

d) utilising the group of antibodies to deplete molecules from the test sample, to increase the relative abundance of a molecule having a low relative abundance in the test sample.

In ninth aspect, the invention provides a process for increasing the relative abundance of a molecule having a low relative abundance in a test sample. The process includes the following steps:

a) fractionating the test sample according to a property of the molecules of the test sample, to form at least two fractions of the test sample;

b) providing a first population of hosts for producing a first group of antibodies for binding to molecules of the test sample that have a high relative abundance in each fraction of the test sample;

c) introducing each fraction of the test sample into a host of the first population so that each host of the first population receives one of the fractions of the test sample, to produce the first group of antibodies;

d) utilising the first group of antibodies to deplete molecules from the test sample, to produce a first depleted sample;

e) fractionating the first depleted sample according to a property of the molecules of the first depleted sample to form at least two fractions of the first depleted sample;

f) providing a second population of hosts for producing a second group of antibodies for binding to molecules of the test sample that have a high relative abundance in each fraction of the first depleted sample;

g) introducing each fraction of the first depleted sample into a host of the second population so that each host of the second population receives one of the fractions of the first depleted sample, to produce the second group of antibodies;

h) utilising the first group of antibodies and the second group of antibodies to deplete molecules from the test sample, to increase the relative abundance of a molecule having a low relative abundance in the test sample.

In a tenth aspect, the invention provides a process for producing a purified form of a molecule having a low relative abundance in a test sample. The process includes the following steps:

a) fractionating the test sample according to a property of the molecules of the test sample, to form at least two fractions of the test sample;

b) providing a population of hosts for producing a group of antibodies for binding to molecules of the test sample that have a high relative abundance in each fraction of the test sample;

c) introducing each fraction of the test sample into a host of the population so that each host of the population receives one of the fractions of the test sample, to produce the group of antibodies;

d) utilising the group of antibodies to deplete molecules from the test sample, to produce a purified form of a molecule having a low relative abundance in a test sample.

In an eleventh aspect, the invention provides a process for producing a purified form of a molecule having a low relative abundance in a test sample. The process includes the following steps:

a) fractionating the test sample according to a property of the molecules of the test sample, to form at least two fractions of the test sample;

b) providing a first population of hosts for producing a first group of antibodies for binding to molecules of the test sample that have a high relative abundance in each fraction of the test sample;

c) introducing each fraction of the test sample into a host of the first population so that each host of the first population receives one of the fractions of the test sample, to produce the first group of antibodies;

d) utilising the first group of antibodies to deplete molecules from the test sample, to produce a first depleted sample;

e) fractionating the first depleted sample according to a property of the molecules of the first depleted sample to form at least two fractions of the first depleted sample;

f) providing a second population of hosts for producing a second group of antibodies for binding to molecules of the test sample that have a high relative abundance in each fraction of the first depleted sample;

g) introducing each fraction of the first depleted sample into a host of the second population so that each host of the second population receives one of the fractions of the first depleted sample, to produce the second group of antibodies;

h) utilising the first group of antibodies and the second group of antibodies to deplete molecules from the test sample, to produce a purified form of a molecule having a low relative abundance in a test sample.

In a twelfth aspect, the invention provides a purified form of a molecule. The purified form of the molecule is characterised in being one produced by the process of the eleventh aspect of the invention.

In a thirteenth aspect, the invention provides a kit or composition for detecting a ligand or binding partner for a molecule having a low relative abundance in a test sample. The kit includes a purified form of the molecule according to the twelfth aspect of the invention. The purified form of the molecule may be arranged on a solid phase.

In a fourteenth aspect, the invention provides a process for producing an antibody that binds to a molecule having a low relative abundance in a test sample. The process includes the following steps:

a) producing a sample according to the process of the eleventh aspect of the invention; and b) utilising the sample to produce the antibody.

In a fifteenth aspect, the invention provides an antibody that binds to a molecule having a low relative abundance in a test sample. The antibody is characterised in being one produced by the process of the fourteenth aspect of the invention.

In a sixteenth aspect, the invention provides a kit or composition for detecting a molecule having a low relative abundance in a target sample. The kit includes an antibody according to the fifteenth aspect of the invention. The antibody may be arranged on a solid phase.

DETAILED DESCRIPTION OF THE EMBODIMENTS

Figure 1:
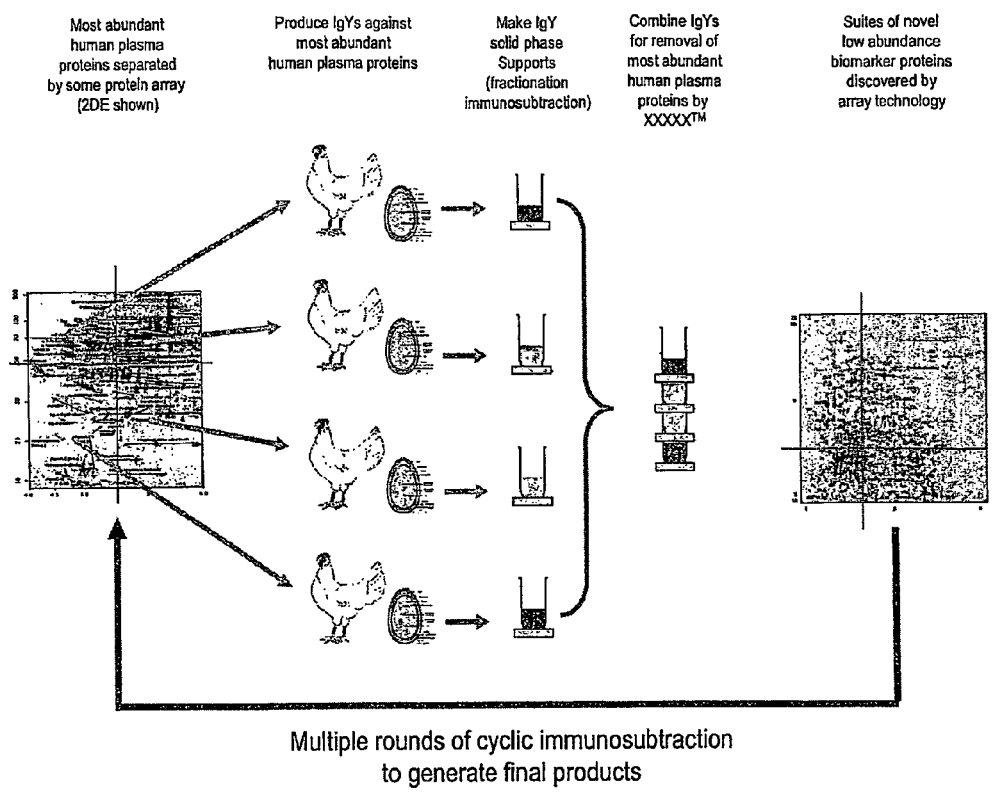
FIG. 1. A representation of a preferred process of the invention for increasing the relative abundance of molecules.
Figure 2:
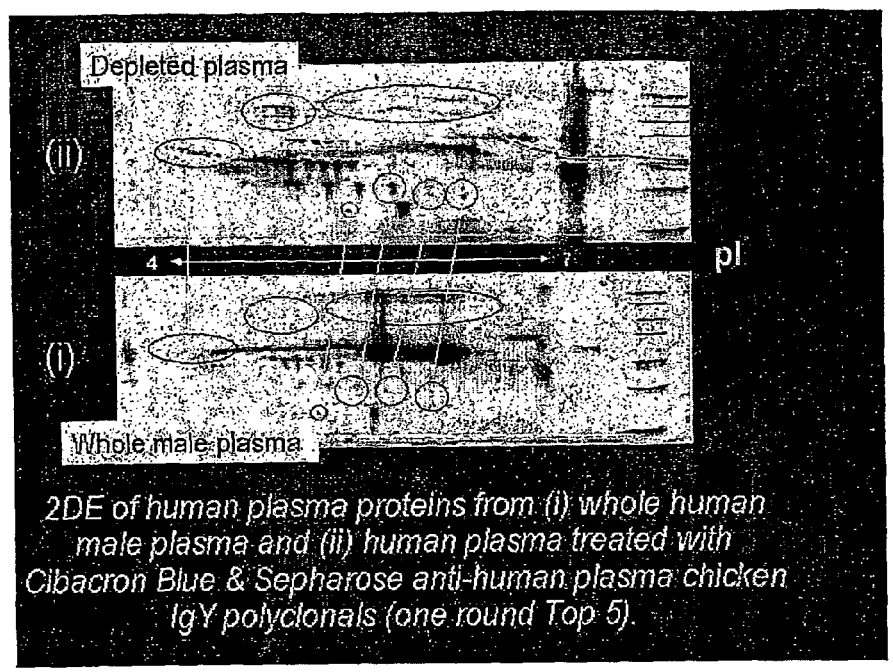
FIG. 2. 2 dimensional electrophoresis gel showing removal of high abundance proteins.
Figure 3A:
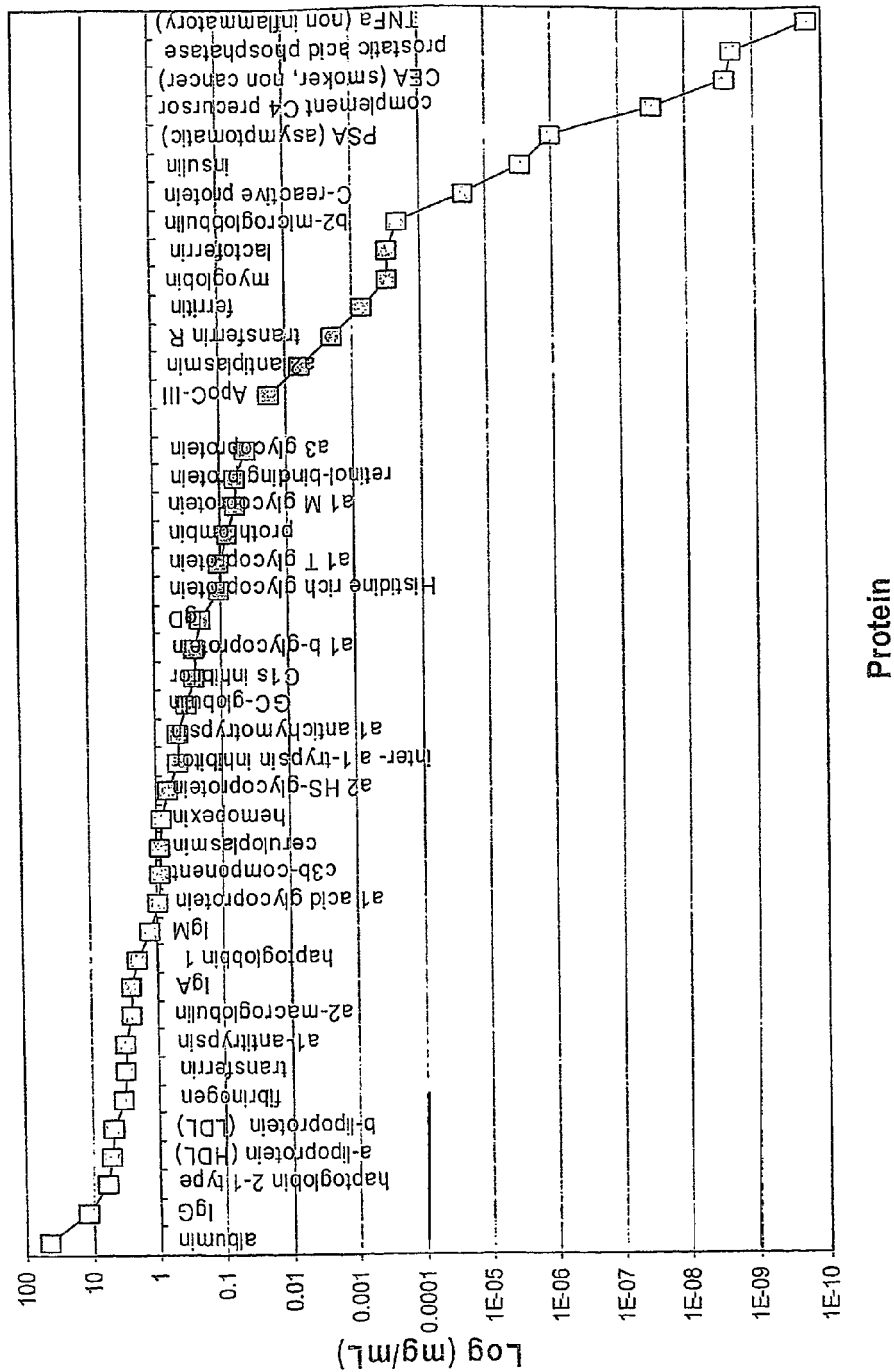
FIG. 3. (3A) A graphical representation of the concentration of proteins in plasma. (3B) A graphical representation of the concentration of proteins in plasma. The area marked by the dashed box indicates plasma proteins that can be visualised by 2 dimensional gel electrophoresis without immunodepletion, or in other words without immunosubtraction. (3C) A graphical representation of the concentration of proteins in plasma. The area marked by the dashed box in the lower right corner indicates the immunodepletion required to identify proteins having a low relative abundance. (3D) A graphical representation of the concentration of proteins in plasma. The filled in box marked "1" represents plasma proteins that are depleted after 1 round of depletion and without fractionation. (3E) A graphical representation of the concentration of proteins in plasma. The filled in boxes marked "1" and "2" represent plasma proteins that are depleted after 2 rounds of depletion and without fractionation. (3F) A graphical representation of the concentration of proteins in plasma. The filled in boxes marked "1", "2" and "3" represent plasma proteins that are depleted after 3 rounds of depletion and without fractionation. (3G) A graphical representation of the concentration of proteins in plasma. The filled in boxes marked "1", "2", "3" and "4" represent plasma proteins that are depleted after 4 rounds of depletion and without fractionation. (3H) A graphical representation of the concentration of proteins in plasma. The filled in boxes marked "1", "2", "3", "4" and "5" represent plasma proteins that are depleted after 5 rounds of depletion and without fractionation. (3I) A graphical representation of the concentration of proteins in plasma. The filled in box marked "1" represents plasma proteins that are depleted after 1 round of depletion and with fractionation. (3J) A graphical representation of the concentration of proteins in plasma. The filled in boxes marked "1" and "2" represent plasma proteins that are depleted after 2 rounds of depletion and with fractionation. (3K) A graphical representation of the concentration of proteins in plasma. The filled in boxes marked "1", "2" and "3" represent plasma proteins that are depleted after 3 rounds of depletion and with fractionation. The representation demonstrates that after 3 rounds of depletion and fractionation, the proteins having a low relative abundance in plasma can be detected.
Figure 3B:
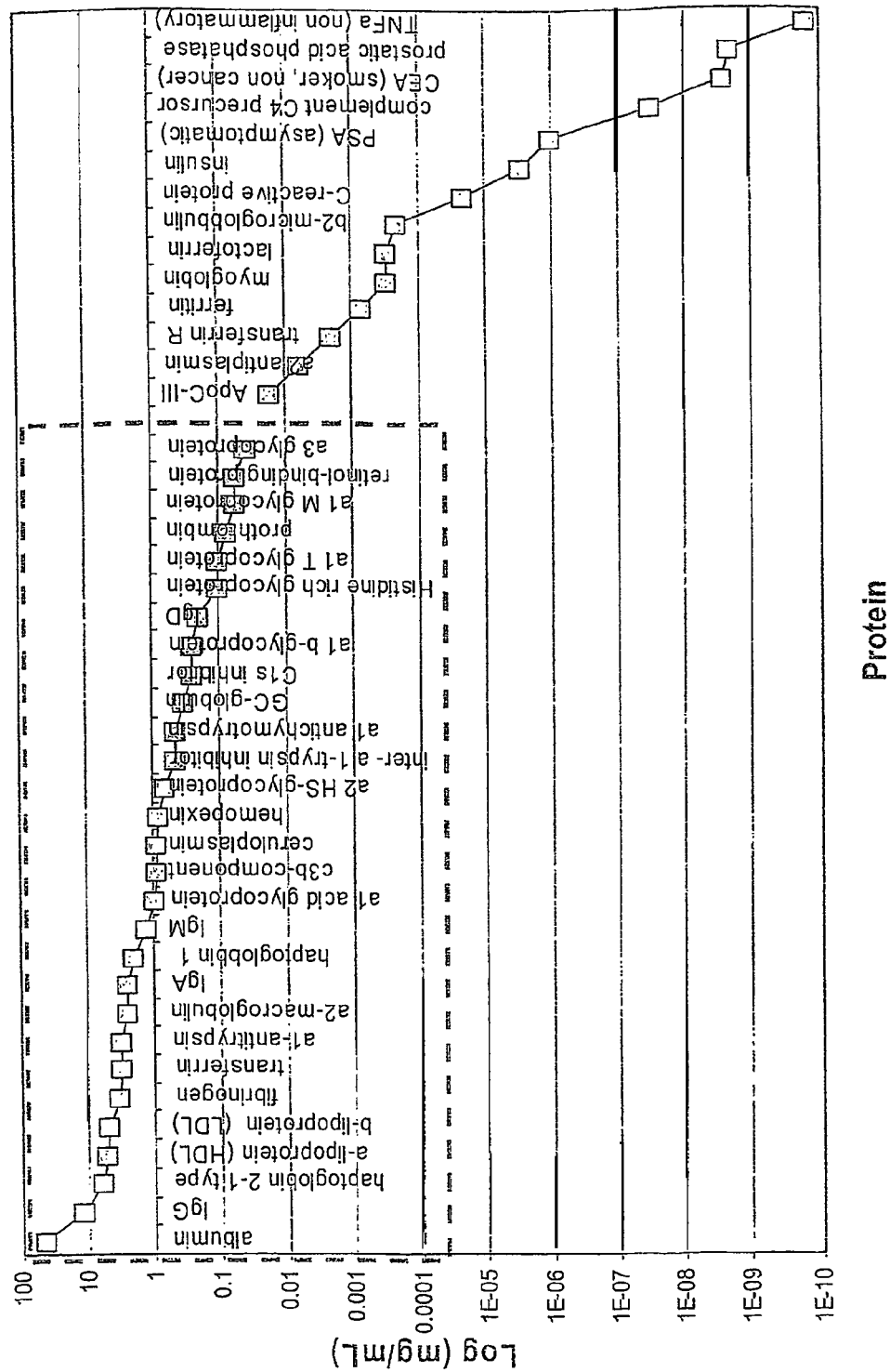
Figure 3C:
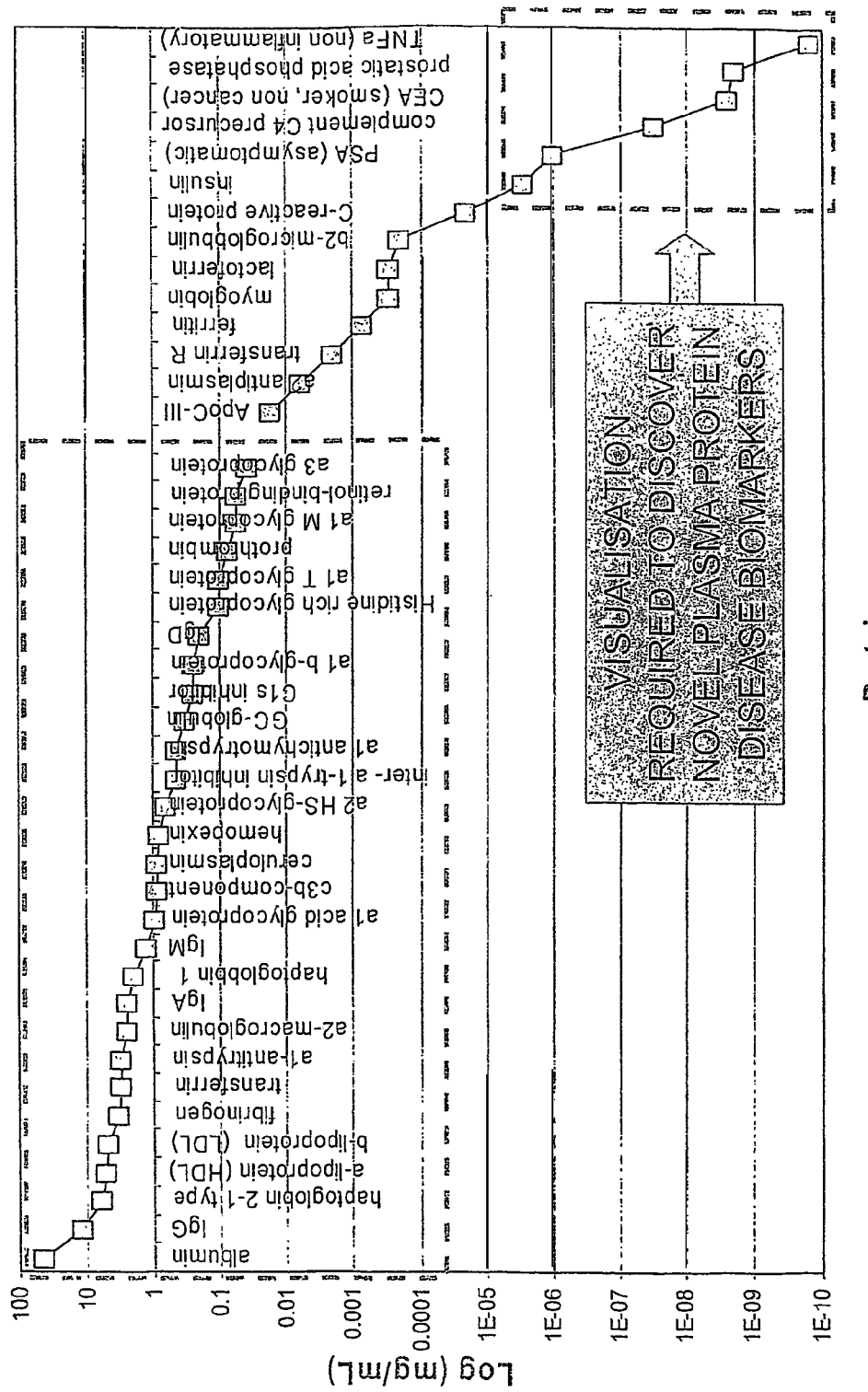
Figure 3D:
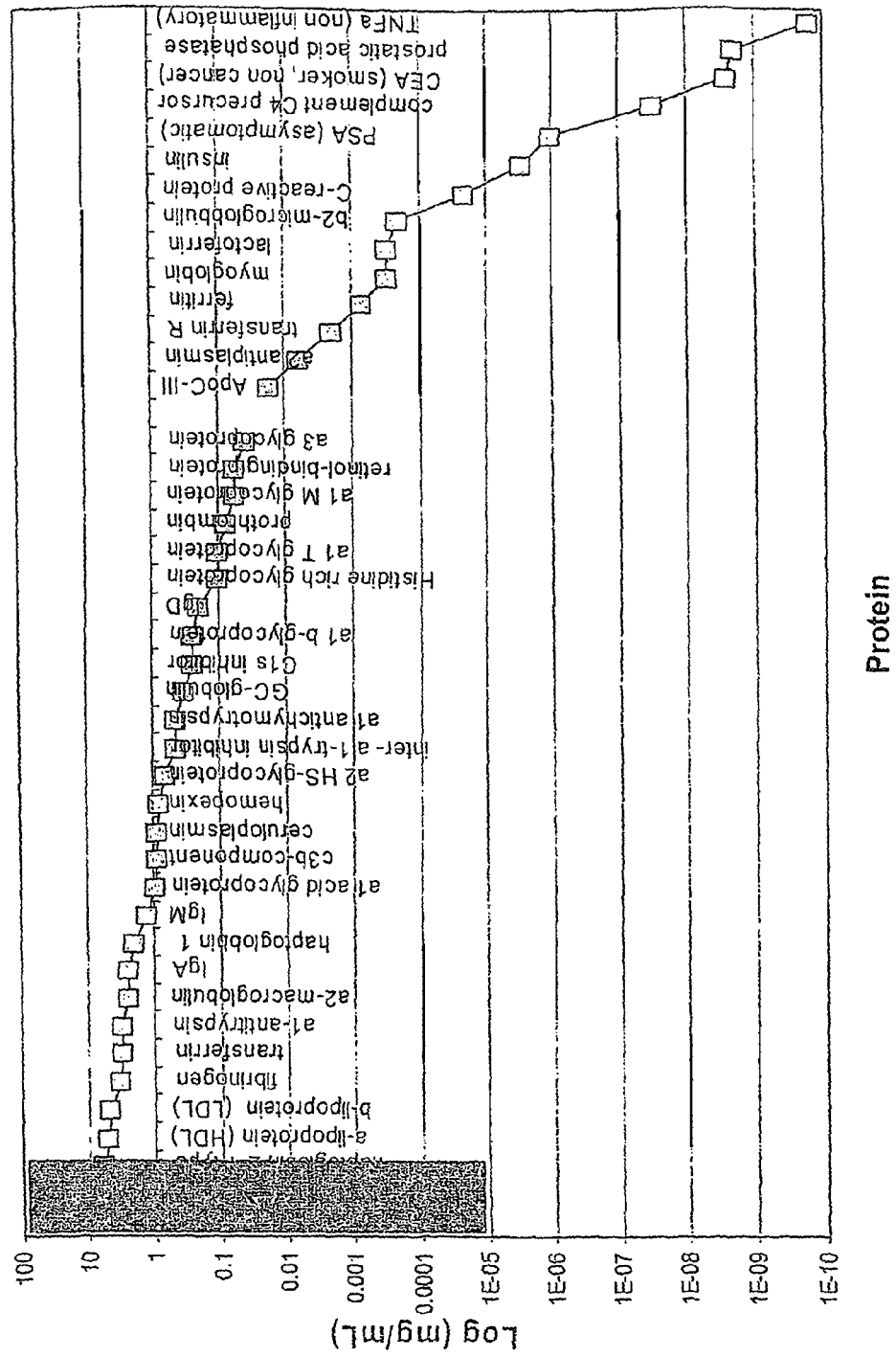
Figure 3E:
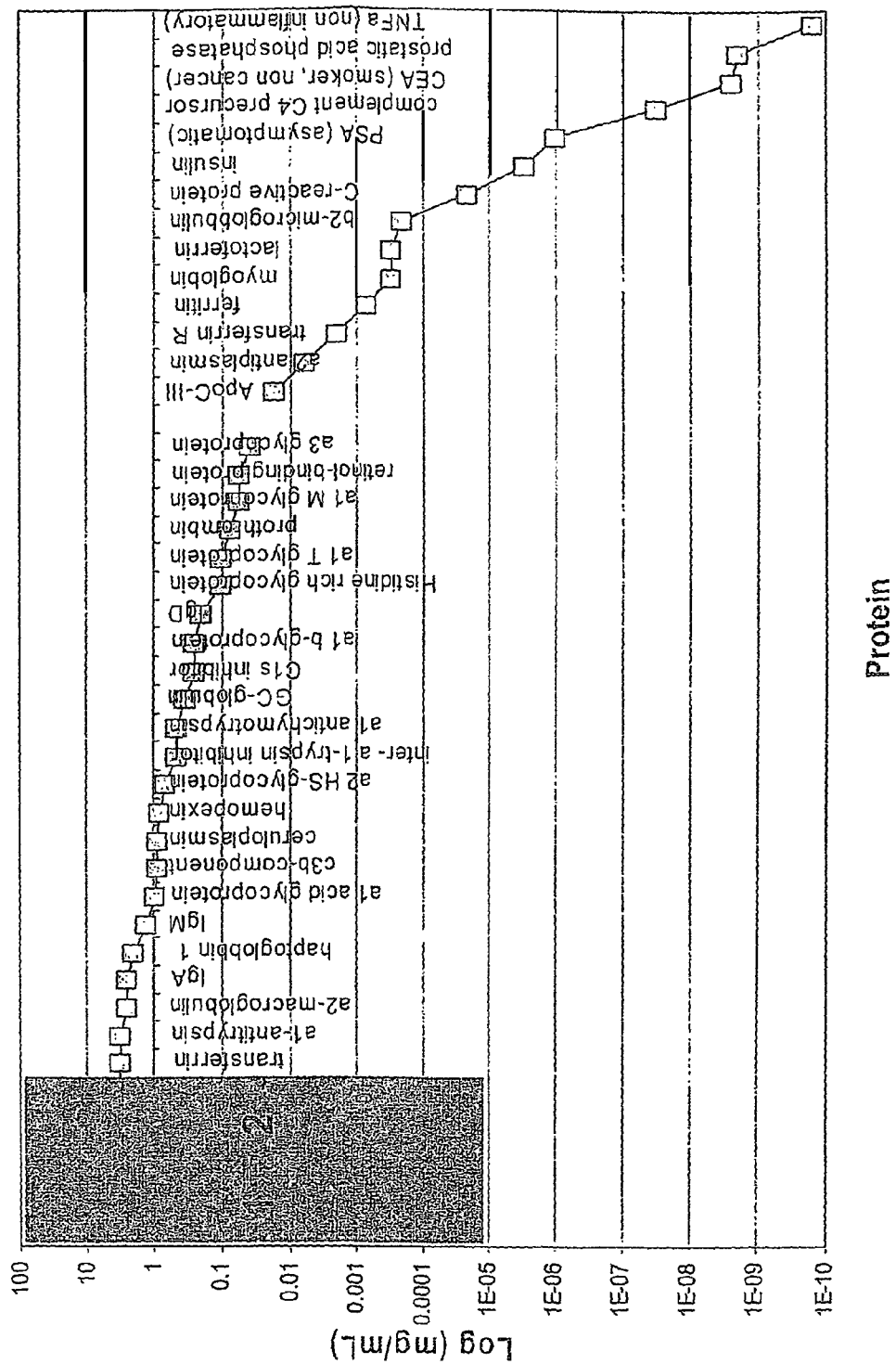
Figure 3F:
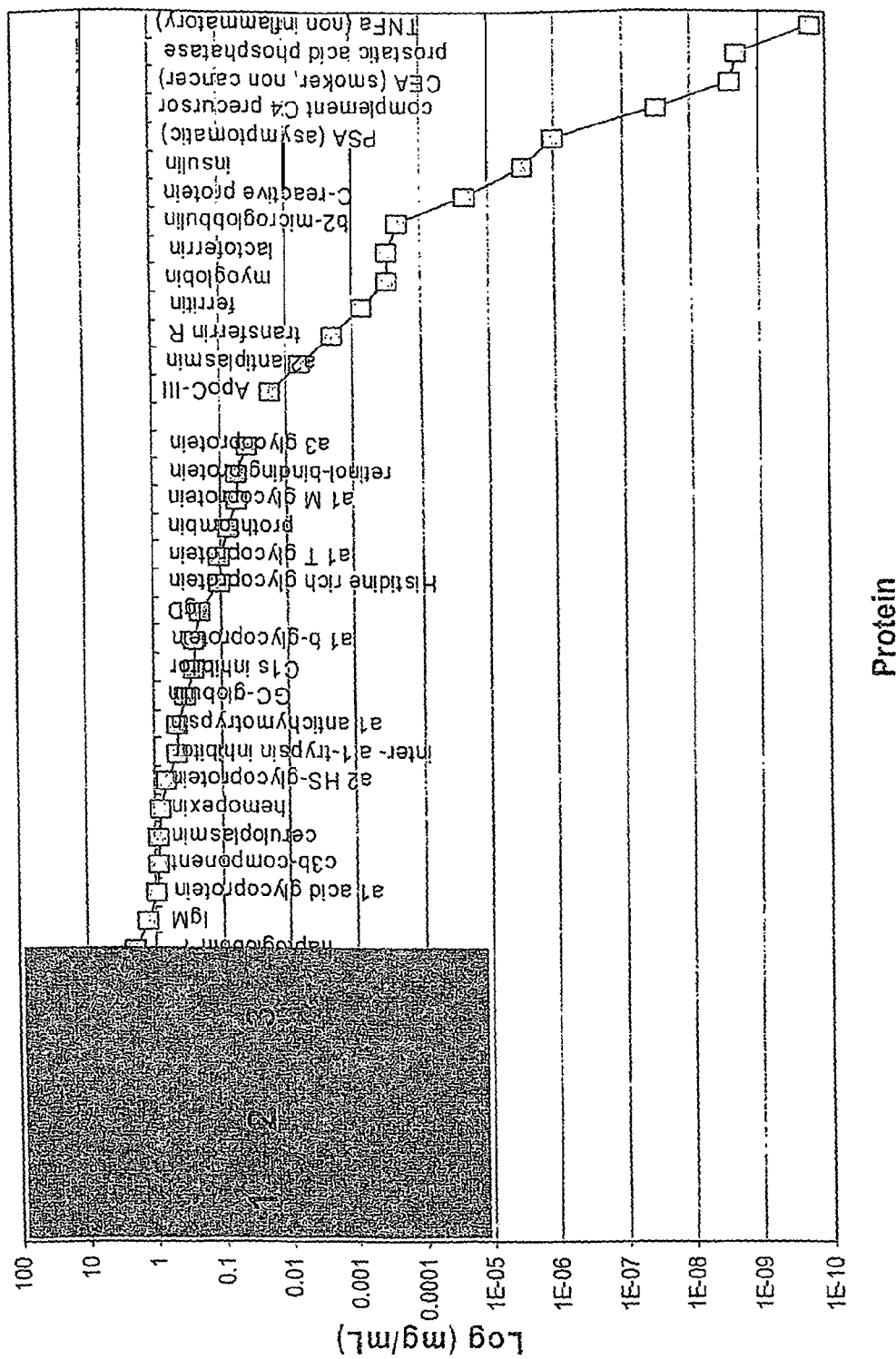
Figure 3G:
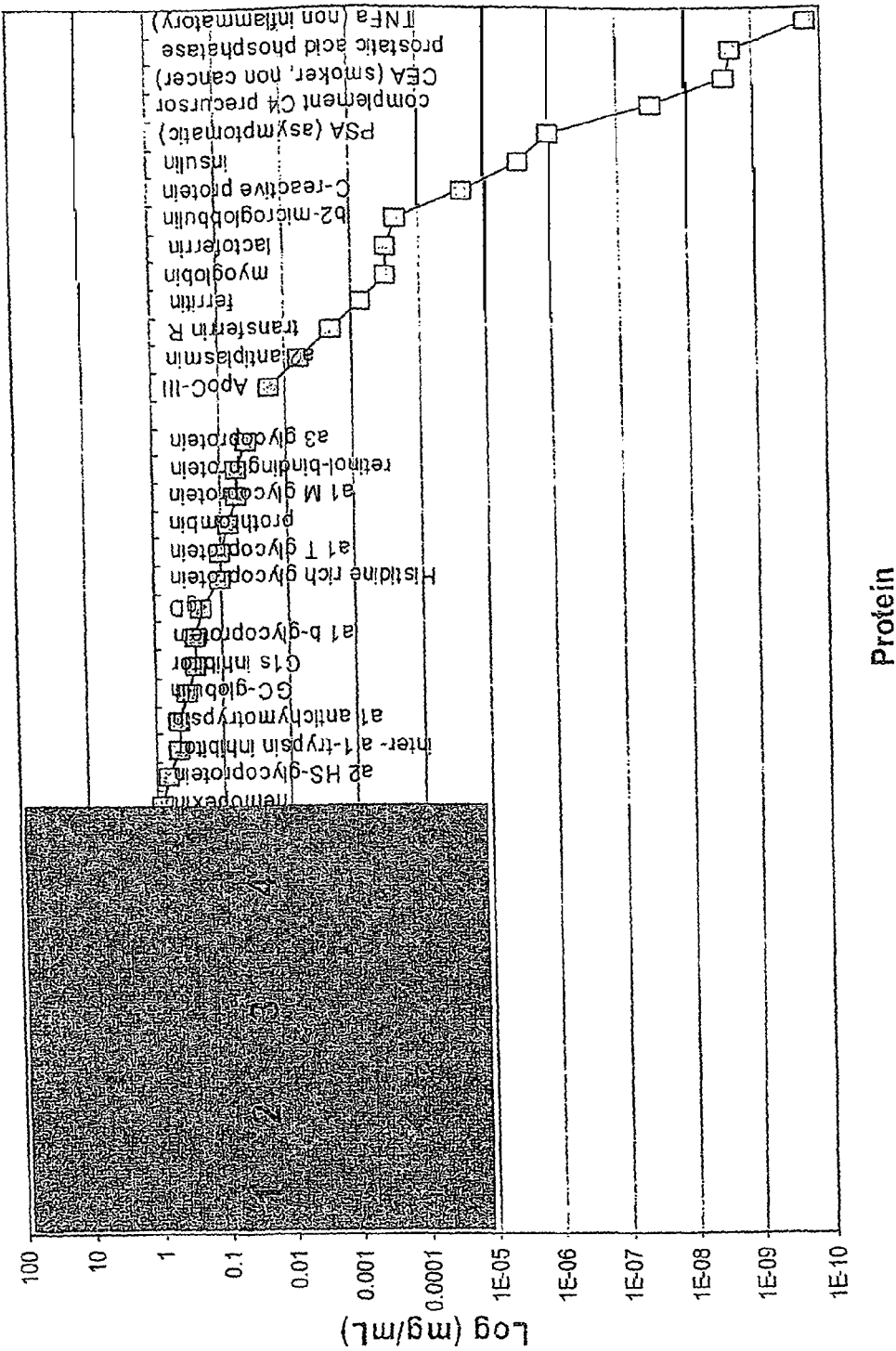
Figure 3H:
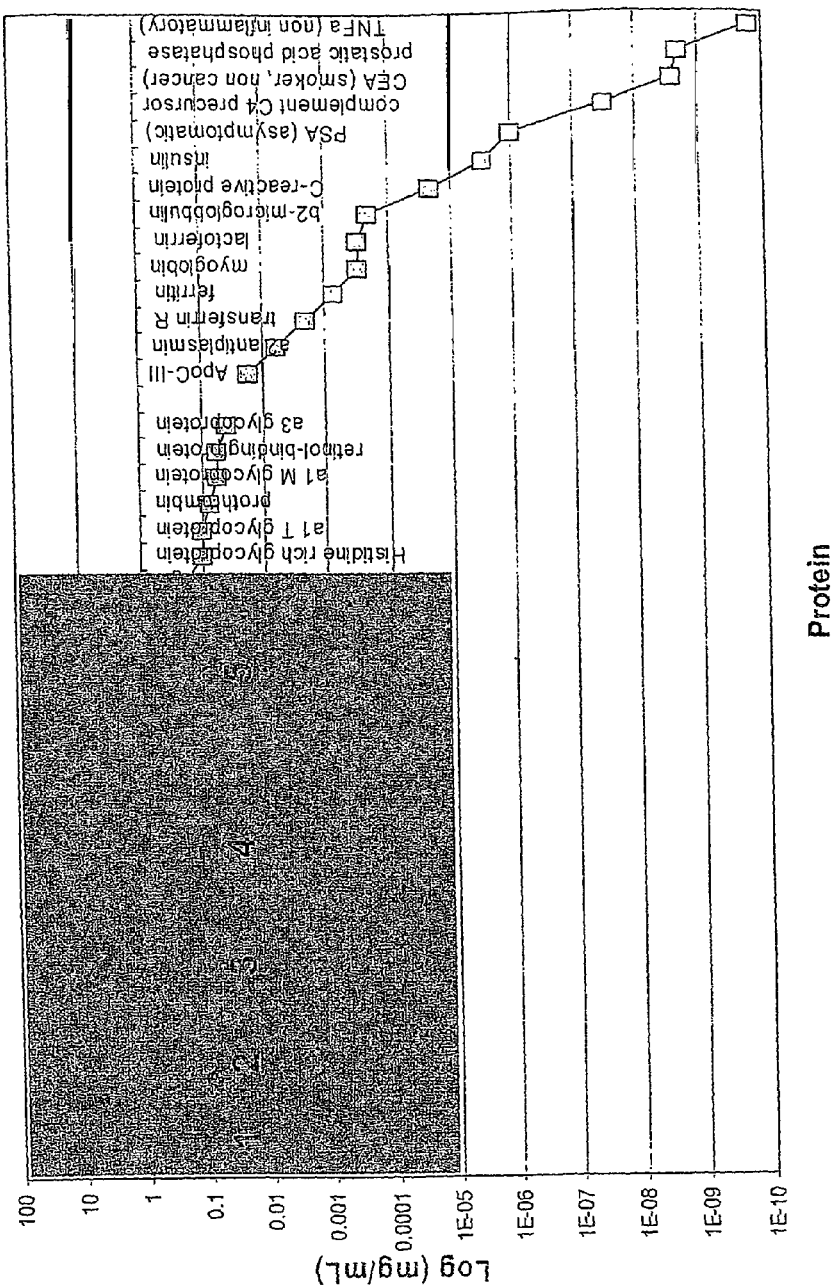
Figure 31:
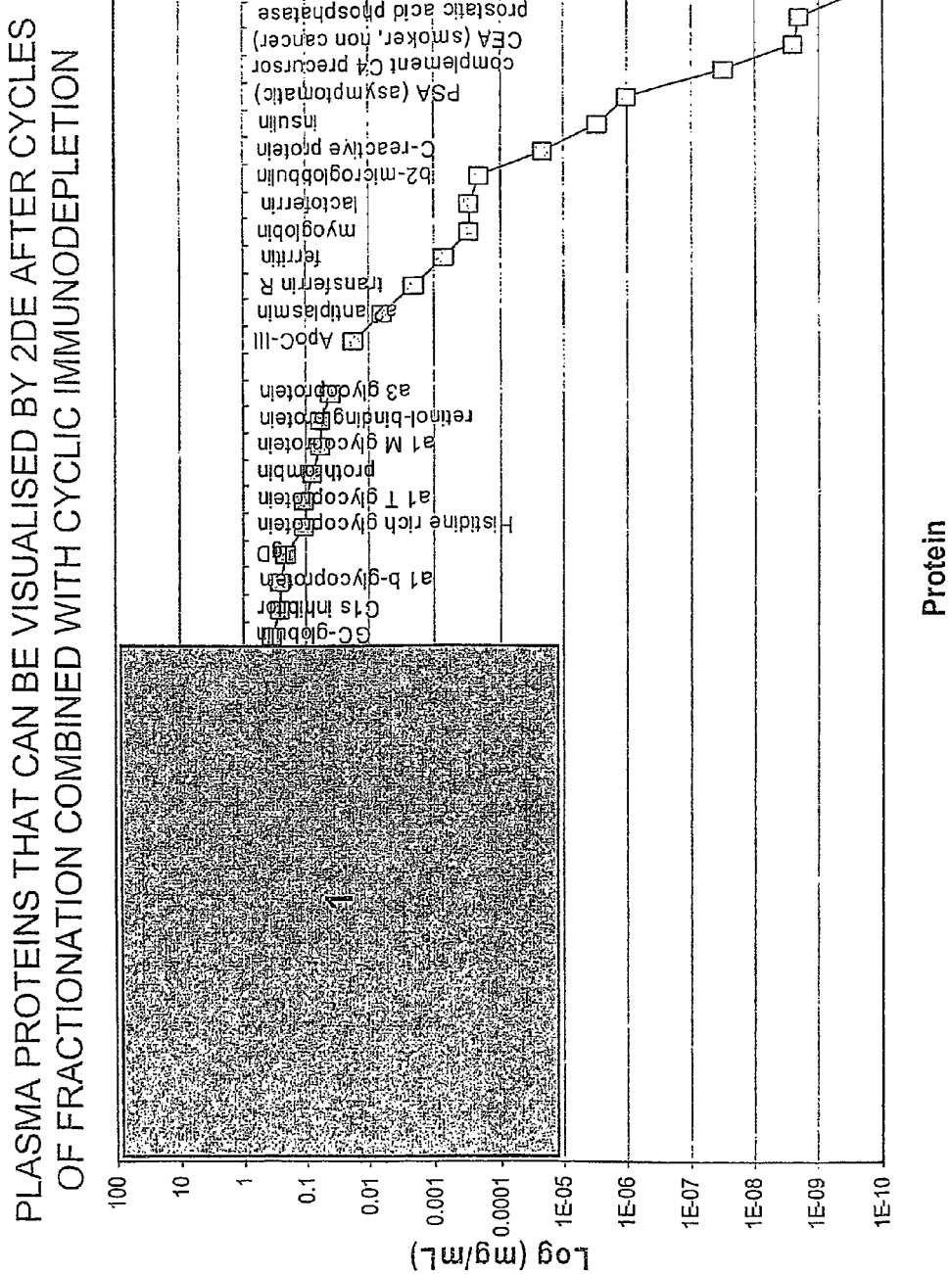
Figure 3J:
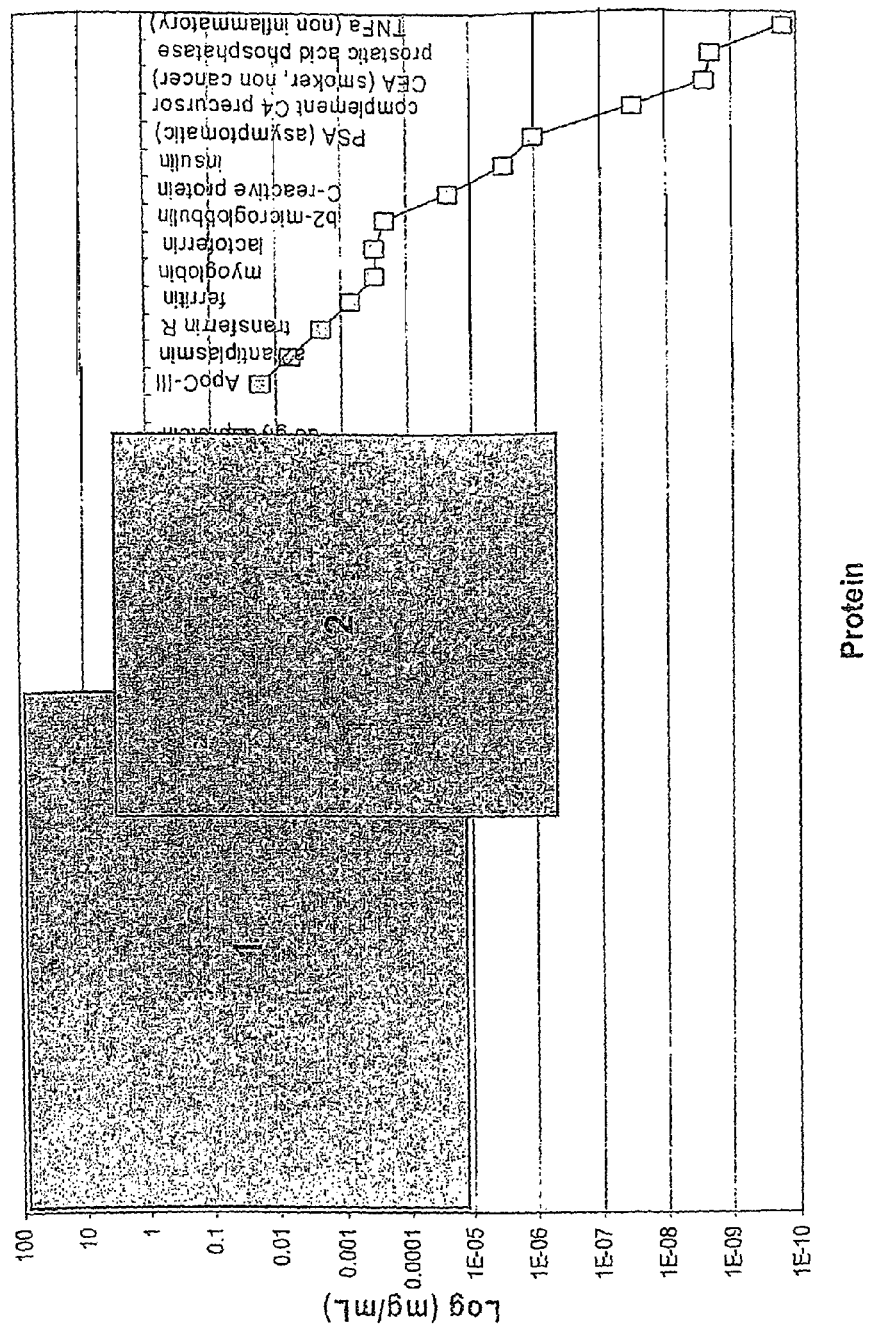
Figure 3K:
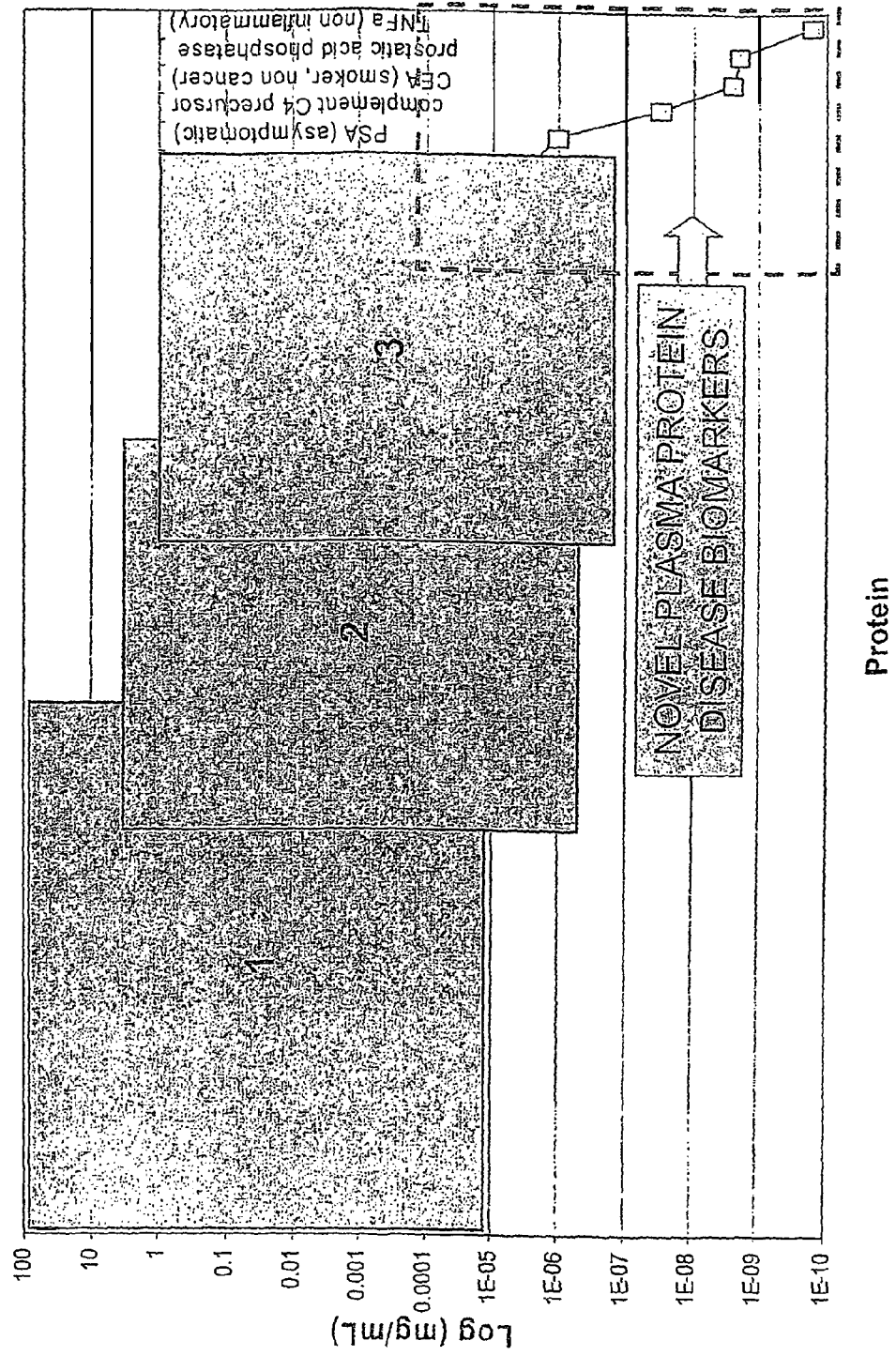

As described herein, the inventor has found that a molecule of interest, such as a target molecule, and particularly those molecules that have a low relative abundance in a test sample, can be identified or detected by depleting molecules from the test sample that have a higher relative abundance, or in other words, a higher relative amount or higher proportion, than the target molecule. By depleting molecules that have a higher relative abundance, the relative abundance of the target molecule in the test sample is increased which in turn improves the ease with which such molecules can be identified or detected.

The increase in the relative abundance of the target molecule is achieved by using the test sample as an immunogen to produce antibodies that are then used to deplete molecules having a higher relative abundance than the target molecule from the test sample. The production of antibodies by immunising with the test sample is particularly advantageous because in the subsequent depletion step, it is possible to deplete molecules having a higher relative abundance from the sample without knowing the identity of these molecules. In other words, there is no need for knowledge of the molecules having a higher relative abundance in the test sample in order to deplete these from the sample. Thus a target molecule comprised in an otherwise poorly characterised test sample can be detected by the process.

A further advantage of using the test sample as an immunogen for producing antibodies that are then used to deplete molecules having a higher relative abundance is that it is possible to generate antibodies that are reactive with different epitopes on the same molecular species. Accordingly, the antibodies provided by the process of the invention tend to have a greater capacity for depletion of high abundance molecules from a test sample.

Thus in one aspect, the invention is a process for increasing the relative abundance of a target molecule in a test sample including:

a) utilising the test sample to produce a first group of antibodies for binding to at least one species of molecule in the test sample that has a higher relative abundance in the sample than the target molecule;

b) utilising the first group of antibodies to deplete from the test sample at least one species of molecule that has a higher relative abundance in the test sample than the target molecule, to produce a first depleted sample;

c) utilising the first depleted sample to produce a second group of antibodies for binding to at least one species of molecule in the first depleted sample that has a higher relative abundance in the first depleted sample than the target molecule;

d) utilising the first and second groups of antibodies to deplete from the test sample at least one species of molecule that has a higher relative abundance in the test sample than the target molecule, to increase the relative abundance of the target molecule in the test sample. This process is referred to herein as "cyclic immunosubtraction".

It will be understood that steps c) and d) of the process are particularly important as the antibodies produced therein permit the depletion of molecules that have a lower relative abundance than the molecules depleted in step b) and yet a higher relative abundance than the target molecule. One particular advantage is that low abundance molecules can be made visible, for example by 2 dimensional gel electrophoresis, by the process.

One particularly important advantage of the process is that it can be performed in a fashion whereby molecules that have a higher relative abundance than the target molecule are sequentially removed in each subsequent depletion step. For example, and as described further herein, the steps of using a sample as an immunogen to produce antibodies that are then used to deplete molecules from a sample that have a higher relative abundance than the target molecule, thereby increasing relative abundance of the target molecule, can be repeated multiple times. Accordingly, molecules having a higher relative abundance are depleted and relative abundance of the molecules having the lower relative abundance is increased.

For example, for producing a third depleted sample, the process may include further steps of:

e) utilising the sample produced by the depletion of the test sample with the first and second groups of antibodies (i.e. utilising a "second depleted sample") to produce a third group of antibodies for binding to at least one species of molecule in the second depleted sample that has a higher relative abundance in the second depleted sample than the target molecule; and f) utilising the first, second and third groups of antibodies to deplete from the test sample at least one species of molecule that has a higher relative abundance in the test sample than the target molecule, to produce a third depleted sample.

Thus it will be understood that the sample produced from the depletion of the test sample with the first and second groups of antibodies, or the first pool of antibodies, can be used to produce third and further groups of antibodies, which can be used sequentially with the first and second groups of antibodies, or in a composition including the first pool of antibodies, to produce further depleted samples in which the relative abundance of the target molecule is increased.

It will be understood that the first and second groups of antibodies may be used sequentially to deplete from the test sample the at least one species of molecule that has a higher relative abundance in the test sample than the target molecule. In an alternative process, the first and second groups of antibodies are combined as in the form of a composition and the composition is then used to deplete from the test sample at least one species of molecule that has a higher relative abundance in the test sample than the target molecule.

Thus in another aspect, the invention provides a process for increasing the relative abundance of a target molecule in a test sample including:

a) utilising the test sample to produce a first group of antibodies for binding to at least one species of molecule in the test sample that has a higher relative abundance in the sample than the target molecule;

b) utilising the first group of antibodies to deplete from the test sample at least one species of molecule that has a higher relative abundance in the test sample than the target molecule, to produce a first depleted sample;

c) utilising the first depleted sample to produce a second group of antibodies for binding to at least one species of molecule in the first depleted sample that has a higher relative abundance in the first depleted sample than the target molecule;

d) combining the first and second group of antibodies to form a first pool of antibodies; and e) utilising the first pool of antibodies to deplete from the test sample at least one species of molecule that has a higher relative abundance in the test sample than the target molecule, to increase the relative abundance of the target molecule in the test sample.

It will be understood that the sample produced from the depletion of the test sample with the first pool of antibodies, can be used to produce third and further groups of antibodies, which can be used sequentially with the first and second groups of antibodies, or in a composition including the first pool of antibodies, to produce further depleted samples in which the relative abundance of the target molecule is increased.

Thus where the process includes the step of forming a first pool of antibodies for use in depleting a species of molecule that has a higher relative abundance than the target molecule in the test sample, the process includes the further steps of:

f) utilising the sample produced by the depletion of the test sample with the first pool of antibodies (i.e. utilising a "second depleted sample") to produce a third group of antibodies for binding to at least one species of molecule in the second depleted sample that has a higher relative abundance in the second depleted sample than the target molecule; and g) utilising the first pool of antibodies and the third group of antibodies to deplete from the test sample at least one species of molecule that has a higher relative abundance in the test sample than the target molecule, to produce a third depleted sample.

In this embodiment, it will be understood that the first pool of antibodies and the third group of antibodies can be used sequentially, or alternatively, in the form of a composition, for example by combining the first pool of antibodies and the third group of antibodies to form a second pool of antibodies, to deplete from the test sample at least one species of molecule that has a higher relative abundance in the test sample than the target molecule.

It will be understood that one consequence of the depletion of molecules having a higher relative abundance than the target molecule is that in the depleted samples (for example, the first, second and further depleted samples), the amount of molecules is reduced. To maintain an appropriate amount of molecules to produce a group of antibodies to molecules that have a higher relative abundance than the target molecule, typically it is necessary to use the test sample as a source of depleted samples for producing antibodies to molecules that have a higher relative abundance than the target molecule. Alternatively, it may be possible to use a depleted sample as a source for further depleted samples i.e. it may be possible to use the first depleted sample as a source for a second and third depleted sample, or it may be possible to use the second depleted sample as a source for the third depleted sample, and the third depleted sample as a source for a fourth depleted sample and so on.

Thus in another aspect, the invention provides a process for increasing the relative abundance of a target molecule in a sample including:

a) utilising the sample to produce a first group of antibodies for binding to at least one species of molecule in the sample that has a higher relative abundance in the sample than the target molecule;

b) utilising the first group of antibodies to deplete from the sample at least one species of molecule that has a higher relative abundance in the sample than the target molecule, to produce a first depleted sample;

c) utilising the first depleted sample to produce a second group of antibodies for binding to at least one species of molecule in the first depleted sample that has a higher relative abundance in the first depleted sample than the target molecule; and d) utilising the second group of antibodies to deplete from the first depleted sample at least one species of molecule that has a higher relative abundance in the first depleted sample than the target molecule, to increase the relative abundance of the target molecule.

According to this aspect of the invention, it will be understood that the sample produced from the depletion of the first depleted sample with the second group of antibodies (in this aspect of the invention, the "second depleted sample"), can be used to produce third and further groups of antibodies, which can be used to produce further depleted samples in which the relative abundance of the target molecule is increased.

Thus in one embodiment, the process includes the further steps of:

e) utilising the second depleted sample to produce a third group of antibodies for binding to at least one species of molecule in the second depleted sample that has a higher relative abundance in the second depleted sample than the target molecule; and f) utilising the third group of antibodies to deplete from the second depleted sample at least one species of molecule that has a higher relative abundance in the second depleted sample than the target molecule, to produce a third depleted sample.

The process may include further steps of utilising the third depleted sample to produce further groups of antibodies for producing further depleted samples.

The test sample for use in the process of the invention described herein may be processed before use in the process of the invention. For example, the test sample may be fractionated to remove molecules in the sample that have a particular physical characteristic. Thus, the test sample may be fractionated to remove molecules in the sample that have a particular molecular weight, hydrophobicity and/or molecular charge. Molecular weight chromatography, for example, using gel exclusion columns, anion exchange chromatography, isoelectric focussing or 2 dimensional gel electrophoresis could be used for this purpose.

Alternatively, the test sample may be fractionated to remove molecules that have a particular epitope. For example, the test sample may be contacted with one or more antibodies that bind to one or molecules in the test sample, to remove these molecules from the test sample. Examples of these antibodies include antibodies that bind to albumin, IgG, transferrin, haptoglobin, alpha 1 antitrypsin, alpha 2 macroglobulin, IgA, IgM, alpha 1 acid glycoprotein, hemopexin, alpha 2 HS glycoprotein, alpha 1 antichymotrypsin, transhyretin and apo A1 lipoprotein. US patent application No. 2002/0127739A describes a suitable immunosubtraction procedure for removing molecules that have a particular epitope.

Where the test sample contains glycoprotein, the test sample may be treated to remove carbohydrate.

Further, samples produced by the depletion of molecules having a higher relative abundance than the target molecule, for example the "first-", "second-", "third-" or "further depleted samples" could be processed as described above.

The test sample may be utilised to produce antibodies for binding to at least one molecule that has a higher relative abundance in the sample than the target molecule by immunising an organism with the whole of the test sample. Alternatively, one or more portions only may be used to immunise an organism. These portions may be prepared by a chromatographic procedure described above or other separation procedure. Still further, the test sample may be divided into portions, an organism immunised with a single portion, and antibodies collected from each organism so immunised and combined to produce the group of antibodies for depleting a molecule that has a higher relative abundance in the sample than the target molecule.

Further, samples produced by the depletion of molecules having a higher relative abundance than the target molecule, for example the "first-", "second-", "third-" or "further depleted samples" may be immunised as a whole as described above, or they may be immunised as a portion of the whole, using the chromatographic procedures described above.

Consistent with the preceding paragraphs, the inventor has found that it is particularly advantageous to combine cyclic immunosubtraction with prior fractionation, as described in the preceding paragraphs, because by this approach it is possible to produce an antisera that contains more antibody specificities and therefore, it is possible to produce an antisera that is capable of removing more higher relative abundance molecules from a test sample in each depletion step. Specifically, while not intending to limit the scope of the invention, the inventor believes that with immunisation of an unfractionated test sample, the antibodies that are produced tend to be those that bind to the 2 to 3 species of most abundant molecules in the test sample. Accordingly, in each depletion, only 2 to 3 species of higher relative abundance molecules are removed from the test sample.

From this, the inventor has reasoned that by introducing fractions of a test sample into a host so that each host receives one fraction, it should be possible to raise antibodies to many more species of higher relative abundance molecules in the test sample, because the antibodies produced in each host would bind to the 2 to 3 most abundant species of molecules in each fraction. Accordingly, where the test sample is fractionated into 2 fractions, 2 hosts are immunised, one host with one of the fractions and the other host with the other fraction, so that antibodies will be produced against 2 to 3 species of the most abundant molecules of the test sample in each host. Thus in total, 4 to 6 species of the high relative abundance molecules of the sample can be removed in the first depletion, instead of 2 to 3 species, as would otherwise occur where cyclic immunosubtraction is not combined with fractionation.

It will be understood that the greater the number of fractions, the greater number species of higher relative abundance molecules that can be removed in each depletion. For example, where the test sample is fractionated into 10 fractions, 10 hosts are immunised, each host with one of the fractions, so that antibodies will be produced against 2 to 3 species of the most abundant molecules of each fraction in each host. When these antibodies are used to deplete higher relative abundance molecules, 20 to 30 species of these molecules can be removed in one depletion.

Thus, the inventor has recognised that the very process of fractionating the test sample increases the relative abundance of molecules in each fraction so obtained. It is for this reason that the relative abundance of a target molecule in a sample can be markedly increased when fractionation is combined with cyclic immunosubtraction.

The inventor believes that by combining cyclic immunosubtraction with fractionation, fewer depletion steps are required to increase the relative abundance of a target molecule in a test sample. This means that less time and expense is required to detect, identify or purify these molecules. This is clearly an important advantage of this invention.

Thus in one aspect, the invention is a process for increasing the relative abundance of a molecule having a low relative abundance in a test sample including:

a) fractionating the test sample according to a property of the molecules of the test sample, to form at least two fractions of the test sample;

b) providing a first population of hosts for producing a group of first antibodies for binding to molecules of the test sample that have a high relative abundance in each fraction of the test sample;

c) introducing each fraction of the test sample into a host of the first population so that each host of the first population receives one of the fractions of the test sample, to produce the first group of antibodies;

d) utilising the first group of antibodies to deplete molecules from the test sample, to increase the relative abundance of a molecule having a low relative abundance in the test sample.

Typically the process includes the further steps of:

e) fractionating the first depleted sample according to a property of the molecules of the first depleted sample to form at least two fractions of the first depleted sample;

f) providing a second population of hosts for producing a second group of antibodies for binding to molecules of the test sample that have a high relative abundance in each fraction of the first depleted sample;

g) introducing each fraction of the first depleted sample into a host of the second population so that each host of the second population receives one of the fractions of the first depleted sample, to produce the second group of antibodies;

h) utilising the first group of antibodies and the second group of antibodies to deplete molecules from the test sample, to increase the relative abundance of a molecule having a low relative abundance in the test sample.

It does not matter how many fractions are formed by fractionating the samples used in the process because as discussed above, the mere combination of fractionation with cyclic immunosubtraction has significant advantages for increasing the relative abundance of a target molecule in a sample over mere cyclic immunosubtraction. However, it will also be clear that the more fractions produced, the greater the power of the process to increase the relative abundance of a target molecule in a sample. Typically the test sample or other samples used in the process (for example, the first depleted sample) are fractionated to produce at least 10 fractions, although they may be fractionated to obtain fewer or more fractions than this.

It will be recognised that it is not necessary that all samples used in the process are to be fractionated into the same numbers of fractions. For example, it is not necessary that both the test sample, the first depleted sample, and subsequent depleted samples (if any) need to be fractionated 10 times each. Indeed in some circumstances, it is recognised that it may be more useful to fractionate some samples into greater numbers than others. For example, a test sample may be fractionated into 10 fractions, the first depleted sample may then be fractionated into 5 samples and the second depleted sample fractionated into 3 samples.

Further, as noted above, it is not necessary that all fractions obtained by fractionating the samples used in the process are to be used to raise antibodies for subsequent depletion.

As noted above, the samples used in the process are fractionated according to a property of the molecules of the sample. In other words, the samples may be fractionated to remove molecules in the sample that have a particular physical characteristic. Thus, the sample may be fractionated to remove molecules in the sample that have a particular molecular weight, hydrophobicity, sugar or carbohydrate complexity and/or molecular charge. Molecular weight chromatography, for example, using gel exclusion columns, anion exchange chromatography, isoelectric focussing or 2 dimensional gel electrophoresis could be used for this purpose.

One important consideration in deciding whether to fractionate according to these properties, and the conditions for doing so, is that of the amount of protein or antigen to be obtained in the fractions. Generally speaking, one should seek to provide roughly the same amount of protein in each fraction. To do so, the molecules in the sample could be analysed by 2 dimensional gel electrophoresis and fractionated according to the relative protein distribution observed in each fraction.

It will be understood that it is not necessary to fractionate each sample according to the same property. For example, the test sample could be fractionated according to molecular weight, a first depleted sample could be fractionated according to molecular charge, and subsequent depleted samples could be fractionated according to hydrophobicity.

It will be understood that steps e) to h) of the process are particularly important as the antibodies produced therein permit the depletion of molecules that have a lower relative abundance than the molecules depleted in step d) and yet a higher relative abundance than the molecule having a low relative abundance in the test sample. One particular advantage is that low abundance molecules can be made visible, for example by 2 dimensional gel electrophoresis, by the process.

One particularly important advantage of the process is that it can be performed in a fashion whereby molecules that have a higher relative abundance than the target molecule are sequentially removed in each subsequent depletion step. For example, and as described further herein, the steps of using fractions of a sample as an immunogen to produce antibodies that are then used to deplete molecules from a sample that have a high relative abundance, thereby increasing relative abundance of a molecule that has a low relative abundance in the test sample, can be repeated multiple times. Accordingly, molecules having a higher relative abundance are depleted and the relative abundance of the molecules having the lower relative abundance is increased.

For example, for producing a third depleted sample, the process may include further steps of:

i) fractionating the sample produced by the depletion of the test sample with the first and second groups of antibodies (i.e. fractionating a "second depleted sample") according to a property of the molecules of the second depleted sample to form at least two fractions of the second depleted sample;

j) providing a third population of hosts for producing a third group of antibodies for binding to molecules of the test sample that have a high relative abundance in each fraction of the second depleted sample;

k) introducing each fraction of the second depleted sample into a host of the third population so that each host of the third population receives one of the fractions of the second depleted ample, to produce the third group of antibodies;

l) utilising the first, second and third group of antibodies to deplete molecules from the test sample, to produce a third depleted sample.

It will be understood that the antibodies produced from each host of the population (for example each host of the first population) can be pooled and then the pool of the antibodies used in the depletion step. Alternatively, the antibodies from each host can be used sequentially to deplete the high relative abundance molecules from the test sample.

Further, it will be understood that the sample produced from the depletion of the test sample with the first and second groups of antibodies, or a pool of antibodies as described in the preceding paragraph, can be used to produce third and further groups of antibodies, which can be used sequentially with the first and second groups of antibodies, or in a composition including a pool of antibodies, to produce further depleted samples in which the relative abundance of the target molecule or low relative abundance molecule in the test sample is increased.

It will be understood that the first and second groups of antibodies may be used sequentially to deplete from the test sample the at least one species of molecule that has a higher relative abundance in the test sample than the low relative abundance molecule. In an alternative process, the first and second groups of antibodies are combined as in the form of a composition and the composition is then used to deplete from the test sample at least one species of molecule that has a higher relative abundance in the test sample than the low relative abundance molecule.

Thus in another aspect, the invention provides a process for increasing the relative abundance of a molecule having a low relative abundance in a test sample including:

a) fractionating the test sample according to a property of the molecules of the test sample, to form at least two fractions of the test sample;

b) providing a first population of hosts for producing a first group of antibodies for binding to molecules of the test sample that have a high relative abundance in each fraction of the test sample;

c) introducing each fraction of the test sample into a host of the first population so that each host of the first population receives one of the fractions of the test sample, to produce the first group of antibodies;

d) utilising the first group of antibodies to deplete molecules from the test sample, to produce a first depleted sample;

e) fractionating the first depleted sample according to a property of the molecules of the first depleted sample to form at least two fractions of the first depleted sample;

f) providing a second population of hosts for producing a second group of antibodies for binding to molecules of the test sample that have a high relative abundance in each fraction of the first depleted sample;

g) introducing each fraction of the first depleted sample into a host of the second population so that each host of the second population receives one of the fractions of the first depleted sample, to produce the second group of antibodies;

h) combining the first and second group of antibodies to form a first pool of antibodies;

h) utilising the first pool of antibodies to deplete molecules from the test sample, to increase the relative abundance of a molecule having a low relative abundance in a test sample.

It will be understood that the sample produced from the depletion of the test sample with the first pool of antibodies, can be used to produce third and further groups of antibodies, which can be used sequentially with the first and second groups of antibodies, or in a composition including the first pool of antibodies, to produce further depleted samples.

Thus where the process includes the step of forming a first pool of antibodies for use in depleting a species of molecule that has a higher relative abundance in the test sample, the process includes the further steps of:

i) fractionating the sample produced by the depletion of the test sample with the first pool of antibodies (i.e. fractionating a "second depleted sample") according to a property of the molecules of the second depleted sample to form at least two fractions of the second depleted sample;

j) providing a third population of hosts for producing a third group of antibodies for binding to molecules of the test sample that have a high relative abundance in each fraction of the second depleted sample;

k) introducing each fraction of the second depleted sample into a host of the third population so that each host of the third population receives one of the fractions of the second depleted ample, to produce the third group of antibodies;

l) utilising the first pool of antibodies and the third group of antibodies to deplete molecules from the test sample, to produce a third depleted sample.

In this embodiment, it will be understood that the first pool of antibodies and the third group of antibodies can be used sequentially, or alternatively, in the form of a composition, for example by combining the first pool of antibodies and the third group of antibodies to form a second pool of antibodies, to deplete from the test sample.

The target molecule, or other molecules having a low relative abundance in a sample, are typically proteins. They may or may not be associated with carbohydrate. They are typically single chain proteins, however they may be associated with another peptide chain.

The target molecule may be any molecule capable of raising a humoral immune response. For example, the target molecule may be a carbohydrate, glycolipid or the like. Examples of such molecules include those capable of binding to natural antibodies.

The test sample for use in the process of the invention described herein may be any sample suitable for separation or identification by protein separation or identification techniques such as by 2 dimensional gel electrophoresis. Suitable samples include cell lysates, tissue lysates, organ lysates, organism lysates, body fluid samples, sub-cellular fractions, environmental samples and the like. Soluble fractions are typically used. Suitable fluid samples include cytoplasm, plasma, serum, whole blood, cerebrospinal fluid, synovial fluid, cervico-vaginal fluid and other tissue fluids, organ fluids such as bile, semen and the like; tumours; secretions such as mucinous fluids, exudates, saliva and tears; waste products, such as urine and perspiration and other biological fluids in the case of animals. For plants, micro-organisms and other such organisms, various other fluids, tissues and cell extracts can be used. Thus, plant tissue, such as leaf tissue, can be macerated in a suitable buffer to yield a suitable sample.

Where the sample is derived from an organism, to ensure that the antibodies that are produced are directed against proteins that have a higher relative abundance than the target molecule, it is important that organism used for producing the antibodies is phylogenetically distant from the organism from which the sample is derived. If the phylogenetic distance between the organism from which the sample is derived and the organism to be immunised is too close, antibodies are likely to be produced on the basis of other parameters, including complexity and relative antigenicity of the molecules in the sample.

As described herein, the inventor has found that where the organism from which the sample is derived is mammalian, for example, human and rodent, it is acceptable to use an avian species, such as a chicken to produce antibodies against the sample. The antibodies produced in such an immunisation tend to be those that react with proteins having a high relative abundance. It will be understood that other organisms having the same or greater phylogenetic distance, including other avian species and lizard species could be used.

Typically the species to be immunised with the sample is one that has diverged from the species from which the sample is obtained by at least 1 million years in evolutionary time. For example, an avian species such as a chicken is particularly useful for immunisation with a human derived sample as the divergence of such species is at least 2 million years in evolutionary time.

Examples of particularly useful chicken species and strains include white 1 Leghorn chickens. These are typically about 28 days old at the time of immunisation.

Processes for production and purification of chicken antibodies are known in the art, see for example Tini M. et al. 2002 "Generation and application of chicken egg-yolk antibodies" in Comparative Biochemistry and Physiology Part A 131: 5690574; Fisher M. et al 1996 "Comparison of standard methods for the preparation of egg yolk antibodies: in Tierarztl Prax. 24 (4): 411-8; Akita E M and S. Nakai 1993 in J. Immunol Methods "Comparison of four purification methods for the production of immunoglobulins from eggs laid by hens immunized with an enterotoxigenic *E. coli* strain" 164 (1): 141-142; Cuceanu N. et al. 1991 "Isolation and characterization of egg yolk antibodies IgY from hen immunized with different influenza virus strains" in Roum Arch Microbiol Immunol. 1991 50(3): 215-22; Polson A. 1990 "Isolation of IgY from the yolks of eggs by a chloroform polyethylene glycol procedure" in Immunol Invest 19)3): 253-8; Wallmann J et al. 1990 "A simple method for the isolation of immunoglobulin (y) from eggs of immunised hens" in Zentralbl Veterinarmed B. 37(4):317-20; Chang H et al. 2000 "Isolation of immunoglobulin from egg yolk by anionic polysaccharides" in J Agric Food Chem 48: 995-999; Veroliva A et al. 2000 "Affinity purification of immunoglobulins from chicken egg yolk using a new synthetic ligand" in J Chromatogr B Biomed Sci Appl 749(2): 233-42; Bizhanov G. and G. Vyshniauskis 2000 "A comparison of three methods for extracting IgY from the egg yolk of hens immunized with Sendai virus" in Vet Res Commun 24(2):103-13.

The antibody that is produced by immunisation with the sample and that is to be used for depletion can be of any class, subclass, single chain, and monofunctional, bifunctional or polyfunctional. The antibody can be intact or substantially intact, that is various portions of the antibody can be removed so long as the desired functions, such as antigen binding or Fc receptor binding is retained.

The antibody that is produced by immunisation with the sample and that is to be used for depletion, is a polysera. The polysera may contain antibodies that bind to more than one species of molecule that have a higher relative abundance in the sample than the target molecule. The polysera may contain antibodies that bind to different epitopes on the same species of molecule. The polysera may also contain polyreactive antibodies, that is, antibodies that are cross reactive and accordingly capable of binding to more than one type of epitope.

Examples of high relative abundance molecules that are removed from human serum when the process according to the invention is based on the immunisation of chickens include albumin, IgG, α-lipoprotein, β-lipoprotein, fibrinogen, transferrin, α1-antitrypsin, haptoglobin 2-1 type, α2-macroglobulin, IgA, ceruloplasmin, Ig M, α1 acid glycoprotein, c3-component, hemopexin, α2 HS-glycoprotein, inter-α1-trypsin inhibitor, α1 antichymotrypsin, GC-globulin and IgD. The change in relative abundance accompanied by the depletion of these molecules according to the process of the invention is shown in Table 1.

The antibodies for depleting at least one species of molecule that has a higher relative abundance in the test sample than the target molecule are utilised by contacting the antibodies and the sample in conditions for permitting the antibodies to bind to at least one molecule having higher relative abundance in the sample than the target molecule. It is not necessary that all of the molecules having a higher relative abundance than the target molecule are removed from the sample, and it is not necessary that a species of molecule having a higher relative abundance than the target molecule be completely depleted or otherwise removed from the sample. Accordingly, the conditions for permitting the antibodies to bind to at least one molecule having a higher relative abundance in the sample than the target molecule are those that are sufficient to deplete an amount of the molecule so that the relative abundance of the target molecule is increased in the depleted sample. Examples of these conditions are described further herein. Suitable conditions for this purpose include those described in US 2002/0127739A.

It does not matter whether the antibodies are brought into contact with the sample, or whether the sample is brought into contact with the antibodies, for depletion of molecules having a relative abundance that is higher than the relative abundance of a target molecule in the sample. Typically, the sample is brought into contact with the antibodies.

In one particularly suitable form of the invention, the antibodies are immobilised on a solid phase by adsorption, covalent binding or entrapment in the solid phase, or by attachment to or incorporation on a coating for the solid phase. To facilitate re-use of the antibodies adsorbed on the solid phase, it is preferable that the antibodies are stably bound to the solid phase. Examples of solid phase supports for use in the invention and processes for arranging antibody on the supports are described in US 2002/0127739A. POROS™ (Applied Biosystems, Foster City, Calif.) chromatography media and continuous be matrices such as UNO™ (Bio-Rad Laboratories, Richmond Calif.) are particularly suitable. The solid support may be a matrix made of beads or microbeads of materials such as dextrans, styrenes, agarose, calcium phosphates, acrylics, polyamines, acrylamides or silicas. Once bound to the solid phase, the antibodies may be fixed covalently, for example using bifunctional crosslinking molecules such as glutaraldehyde, dimethyladipindate, dimethyl subserimidate, dimethyl pimlimidate, tetranitromethane and dimethyl 3,3' dithiobisproprionimidate.

It will be understood that the antibody that is produced by immunisation may be utilised with one or more monoclonal antibodies to deplete molecules having a higher relative abundance than a target molecule from a sample. Monoclonal antibodies are powerful reagents because a clone can yield an antibody of high affinity, high avidity or both in essentially unlimited quantity and reproducible quality. Examples of monoclonal antibodies that could be used include antibodies that bind to albumin, IgG, transferrin, haptoglobin, alpha 1 antitrypsin, alpha 2 macroglobulin, IgA, IgM, alpha 1 acid glycoprotein, hemopexin, alpha 2 HS glycoprotein, alpha 1 antichymotrypsin, transthyretin and apo A1 lipoprotein.

Other reagents that could also be used to deplete molecules having a high relative abundance in a sample with the antibodies that are produced by immunisation with the sample include a specific binding partner or any receptor that specifically binds to the molecule having a higher relative abundance or other including lectins such as concanavalin A, wheat germ agglutinin, abrin and so on; metals; co-factors; combinatorial compounds, polymers, nucleic acids, artificial protein sequences and other compounds such as heparin, polymyxin, dyes such as Cibacron blue F3GA and hydrocarbons such as methyl and phenyl radicals that bind hydrophobic proteins, or agents comprising functional groups such as hydrazide, amine, N-hydroxy-succinimide, carboxyl, boronate and organomercury.

Any method that is capable of quantifying an amount of a molecule could be used to determine whether a particular target molecule has been enriched by the process of the invention. Examples of such methods include 2 dimensional gel electrophoresis, western blotting and densitometric analysis of the outputs of these methods. Alternative methods include ELISA and Bradford assay.

By permitting the relative abundance of a target molecule to be increased in a test sample, the process permits improved detection of molecules and provides purified forms of molecules and antibodies that bind thereto. Thus the invention is particularly important for providing process and means for example for detection or diagnosis of quality traits or disease in plants and animals and for detecting contaminants environmental samples, food samples and the like. There now follows a description of uses of the invention for identification, detection or otherwise diagnosis of molecules, and for producing purified forms of low abundance molecules and antibodies thereto.

A. Identifying and Detecting Low Relative Abundance Molecules

In another aspect, the invention provides a process for identifying or detecting a target molecule in a test sample. The process includes the following steps:

a) fractionating the test sample according to a property of the molecules of the test sample, to form at least two fractions of the test sample;

b) providing a first population of hosts for producing a first group of antibodies for binding to molecules of the test sample that have a high relative abundance in each fraction of the test sample;

c) introducing each fraction of the test sample into a host of the first population so that each host of the first population receives one of the fractions of the test sample, to produce the first group of antibodies;

d) utilising the first group of antibodies to deplete molecules from the test sample, to produce a first depleted sample;

e) fractionating the first depleted sample according to a property of the molecules of the first depleted sample to form at least two fractions of the first depleted sample;

f) providing a second population of hosts for producing a second group of antibodies for binding to molecules of the test sample that have a high relative abundance in each fraction of the first depleted sample;

g) introducing each fraction of the first depleted sample into a host of the second population so that each host of the second population receives one of the fractions of the first depleted sample, to produce the second group of antibodies;

h) utilising the first group of antibodies and the second group of antibodies to deplete molecules from the test sample, to identify or detect a target molecule in a test sample.

In another aspect, the invention provides a process for identifying or detecting a target molecule in a test sample. The process includes the following steps:

a) utilising the test sample to produce a first group of antibodies for binding to at least one species of molecule in the test sample that has a higher relative abundance in the sample than the target molecule;

b) utilising the first group of antibodies to deplete from the test sample at least one species of molecule that has a higher relative abundance in the test sample than the target molecule, to produce a first depleted sample;

c) utilising the first depleted sample to produce a second group of antibodies for binding to at least one species of molecule in the first depleted sample that has a higher relative abundance in the first depleted sample than the target molecule;

d) utilising the first and second groups of antibodies to deplete from the test sample at least one species of molecule that has a higher relative abundance in the test sample than the target molecule to produce a second depleted sample; and e) analysing the second depleted sample to detect or identify the target molecule.

According to step e), the second depleted sample can be analysed by 2 dimensional gel electrophoresis, liquid chromatography, mass spectrometry (including ICAT-MS) HPLC, binding assays, staining etc.

To visualise the target molecule, it may be necessary to concentrate or lyophilise the second depleted sample.

B. Producing Purified Forms of Low Relative Abundance Molecules

In another aspect, the invention provides a process for producing a purified form of a target molecule from a test sample. The process includes the following steps:

a) fractionating the test sample according to a property of the molecules of the test sample, to form at least two fractions of the test sample;

b) providing a first population of hosts for producing a first group of antibodies for binding to molecules of the test sample that have a high relative abundance in each fraction of the test sample;

c) introducing each fraction of the test sample into a host of the first population so that each host of the first population receives one of the fractions of the test sample, to produce the first group of antibodies;

d) utilising the first group of antibodies to deplete molecules from the test sample, to produce a first depleted sample;

e) fractionating the first depleted sample according to a property of the molecules of the first depleted sample to form at least two fractions of the first depleted sample;

f) providing a second population of hosts for producing a second group of antibodies for binding to molecules of the test sample that have a high relative abundance in each fraction of the first depleted sample;

g) introducing each fraction of the first depleted sample into a host of the second population so that each host of the second population receives one of the fractions of the first depleted sample, to produce the second group of antibodies;

h) utilising the first group of antibodies and the second group of antibodies to deplete molecules from the test sample, to produce a purified form of a target molecule from a test sample.

In another aspect, the invention provides a process for producing a purified form of a target molecule from a test sample. The process includes the following steps:

a) utilising the test sample to produce a first group of antibodies for binding to at least one species of molecule in the test sample that has a higher relative abundance in the sample than the target molecule;

b) utilising the first group of antibodies to deplete from the test sample at least one species of molecule that has a higher relative abundance in the test sample than the target molecule, to produce a first depleted sample;

c) utilising the first depleted sample to produce a second group of antibodies for binding to at least one species of molecule in the first depleted sample that has a higher relative abundance in the first depleted sample than the target molecule;

d) utilising the first and second groups of antibodies to deplete from the test sample at least one species of molecule that has a higher relative abundance in the test sample than the target molecule, to produce a purified form of the target molecule.

C. Isolating Low Relative Abundance Molecules

Thus the invention provides a process for isolating a target molecule from a sample including:

a) fractionating the test sample according to a property of the molecules of the test sample, to form at least two fractions of the test sample;

b) providing a first population of hosts for producing a first group of antibodies for binding to molecules of the test sample that have a high relative abundance in each fraction of the test sample;

c) introducing each fraction of the test sample into a host of the first population so that each host of the first population receives one of the fractions of the test sample, to produce the first group of antibodies;

d) utilising the first group of antibodies to deplete molecules from the test sample, to produce a first depleted sample;

e) fractionating the first depleted sample according to a property of the molecules of the first depleted sample to form at least two fractions of the first depleted sample;

f) providing a second population of hosts for producing a second group of antibodies for binding to molecules of the test sample that have a high relative abundance in each fraction of the first depleted sample;

g) introducing each fraction of the first depleted sample into a host of the second population so that each host of the second population receives one of the fractions of the first depleted sample, to produce the second group of antibodies;

h) utilising the first group of antibodies and the second group of antibodies to deplete molecules from the test sample, to isolate a target molecule from a sample.

Thus the invention provides a process for isolating a target molecule from a sample including:

a) utilising the test sample to produce a first group of antibodies for binding to at least one species of molecule in the test sample that has a higher relative abundance in the sample than the target molecule;

b) utilising the first group of antibodies to deplete from the test sample at least one species of molecule that has a higher relative abundance in the test sample than the target molecule, to produce a first depleted sample;

c) utilising the first depleted sample to produce a second group of antibodies for binding to at least one species of molecule in the first depleted sample that has a higher relative abundance in the first depleted sample than the target molecule;

d) utilising the first and second groups of antibodies to deplete from the test sample at least one species of molecule that has a higher relative abundance in the test sample than the target molecule, to increase the relative abundance of the target molecule in the test sample; and e) isolating the target molecule from the second depleted sample.

The target molecule may be isolated from the second depleted sample with an antibody. Where an antibody is not available, the target molecule may be isolated by fractionating the second depleted sample, for example by 2 dimensional gel electrophoresis and the cutting the region containing the target molecule from the gel. The target molecule can then be eluted from the gel and used to raise an antibody to the target molecule. Alternatively, the target molecule can be sequenced, peptides can be prepared having regard to the determined sequence and antibodies raised to the peptides.

D. Producing Antibodies to Low Relative Abundance Molecules

The invention also provides a process for producing an antibody that binds to a target molecule having a low relative abundance in a test sample including:

a) producing a sample that has a higher relative abundance of the target molecule than the test sample according to the process of the first aspect of the invention;

b) utilising the produced sample to produce at least one antibody to the target molecule.

It will be understood that where some characteristic of the target molecule is known, the target molecule could be isolated from the sample that has a higher relative abundance of the target molecule, and the isolated molecule could then be used to produce at least one antibody to the target.

Thus in another aspect, the invention provides a process for producing an antibody that binds to a target molecule having a low relative abundance in a test sample including:

a) producing a sample that has a higher relative abundance of the target molecule than the test sample according to the process of the first aspect of the invention;

b) isolating the target molecule from the produced sample; and c) utilising the isolated target molecule to produce at least one antibody to the target molecule.

The invention claimed is:

1. A process for increasing the relative abundance of a molecule having a low relative abundance in a test sample including:

a) fractionating all or a portion of a test sample which includes molecules of high and low relative abundance according to a property of the molecules of the test sample, to form at least two fractions of the test sample;

b) providing a population of hosts for producing a group of antibodies for binding to molecules of the test sample that have a high relative abundance in each fraction of the test sample;

c) introducing each fraction of the test sample into a host of the population so that each host of the population receives one of the fractions of the test sample, to produce the group of antibodies;

d) contacting the group of antibodies produced in step c) with the test sample or a test sample, wherein the antibodies deplete molecules from the test sample or a test sample to produce a first depleted sample having an increased relative abundance of a molecule having a low relative abundance in the test sample or a test sample.

2. The process according to claim 1 including the further steps of:

e) fractionating all or a portion the first depleted sample obtained in step d) according to a property of the molecules of the first depleted sample to form at least two fractions of the first depleted sample;

f) providing a second population of hosts for producing a second group of antibodies for binding to molecules of the test sample that have a high relative abundance in each fraction of the first depleted sample;

g) introducing each fraction of the first depleted sample into a host of the second population so that each host of the second population receives one of the fractions of the first depleted sample, to produce the second group of antibodies;

h) contacting the first group of antibodies produced in step c) and the second group of antibodies produced in step g) with the test sample or a test sample, wherein the antibodies deplete molecules from the test sample or a test sample to produce a second depleted sample having an increased relative abundance of a molecule having a low relative abundance in the test sample or a test sample.

3. The process according to claim 1 wherein the test sample is fractionated to produce at least 10 fractions in step a).

4. The process according to claim 1 wherein not all of the fractions formed in step a) are used in step c).

5. The process according to claim 1 wherein the test sample is fractionated according to at least one of molecular weight, hydrophobicity, carbohydrate complexity and molecular charge of the molecules of the test sample.

6. The process according to claim 1 wherein the test sample is fractionated by at least one of anion exchange chromatography, isoelectric focussing and 2 dimensional gel electrophoresis.

7. The method according to claim 2 wherein the number of fractions formed in steps a) and e) are not the same.

8. The method according to claim 2 wherein the test sample of step a) and the first depleted sample of step e) are fractionated according to different properties of the molecules of these samples.

9. The method according to claim 2 wherein prior to step h), the first group of antibodies and the second group of antibodies are combined to form a pool of antibodies for use in the method of step h).

10. The method according to claim 1 wherein the low abundance molecule is a protein.

11. The method according to claim 1 wherein the test sample is selected from the group consisting of cell lysates, tissue lysates, organ lysates, organism lysates, body fluid samples, sub-cellular fractions and environmental samples.

12. The method according to claim 11 wherein the body fluid sample is selected from the group consisting of cytoplasm, plasma, serum, whole blood, cerebrospinal fluid, synovial fluid, cervico-vaginal fluid, bile, semen, saliva and tears.

13. The method according to claim 1 wherein the species from which the test sample is derived and the species of the host have diverged by at least 1 million years in evolutionary time.

14. The method according to claim 13 wherein the test sample is derived from a mammal and the host is an avian.

15. The method according to claim 14 wherein the avian is a chicken.

16. The method according to claim 2 including the further steps:
   i) fractionating all or a portion of the second depleted sample obtained in step h) according to a property of the molecules of the second depleted sample to form at least two fractions of the second depleted sample;
   j) providing a third population of hosts for producing a third group of antibodies for binding to molecules of the test sample that have a high relative abundance in each fraction of the second depleted sample;
   k) introducing each fraction of the second depleted sample into a host of the third population so that each host of the third population receives one of the fractions of the second depleted ample, to produce the third group of antibodies;
   l) contacting the first, second and third group of antibodies produced in steps c), g) and k) respectively with the test sample or a test sample, wherein the antibodies deplete molecules from the test sample or a test sample to produce a third depleted sample having an increased relative abundance of a molecule having a low relative abundance in the test sample or a test sample.

17. The method according to claim 2 wherein in step h) the first group of antibodies and second group of antibodies are used to deplete molecules from the first depleted sample to form a sample having an increased relative abundance of a molecule having a low relative abundance in the test sample.

18. The method according to claim 1 where in step d), the test sample or a test sample is brought into contact with the group of antibodies to deplete molecules from the test sample.

19. The method according to claim 18 wherein the antibodies are arranged on a solid phase.

20. The method according to claim 19 wherein the antibodies are whole antibodies.

21. The method according to claim 1 wherein prior to step a) or c), the test sample or fraction formed from the test sample are contacted with a reagent for depleting a molecule from the test sample or fraction having a high relative abundance in the test sample or fraction.

22. The method according to claim 21 wherein the reagent is selected from the group consisting of a monoclonal antibody, lectin, metal, co-factor, polymer, nucleic acid, heparin, polymxin and dye.

23. The method according to claim 1 wherein prior to step d) the group of antibodies produced in step c) is combined with a reagent for depleting a molecule from the test sample or a test sample having a high relative abundance in the test sample.

24. The method according to claim 23 wherein the reagent is selected from the group consisting of a monoclonal antibody, lectin, metal, co-factor, polymer, nucleic acid, heparin, polymxin and dye.

25. The method according to claim 24 wherein the antibody is a monoclonal antibody specific for a molecule selected from the group consisting of albumin, IgG, transferin, haptoglobin, alpha 1 antitrypsin, alpha 2 macroglobulin, IgA, IgM, alpha 1 acid glycoprotein, hemopexin, alpha 2 HS glycoprotein, alpha 1 antichymotrypsin, transthyretin and apo A1 lipoprotein.

* * * * *